(12) United States Patent
Chaudhury et al.

(10) Patent No.: US 12,256,759 B2
(45) Date of Patent: Mar. 25, 2025

(54) METHODS FOR THE REDUCTION OF METHANE PRODUCTION IN RUMINANTS

(71) Applicant: Loam Bio Pty Ltd, Orange (AU)

(72) Inventors: Abed Chaudhury, Orange (AU); Karen Paco, St. Paul, MN (US); Michael Anthony Ayliffe, Canberra (AU); Thomas David Loan, Canberra (AU); Ming Luo, Canberra (AU); Tristan Yang, St. Paul, MN (US)

(73) Assignee: Loam Bio Pty Ltd, Orange (AU)

( * ) Notice: Subject to any disclaimer, the term of this patent is extended or adjusted under 35 U.S.C. 154(b) by 0 days.

(21) Appl. No.: 18/291,870

(22) PCT Filed: Aug. 2, 2022

(86) PCT No.: PCT/US2022/039095
§ 371 (c)(1),
(2) Date: Jan. 24, 2024

(87) PCT Pub. No.: WO2023/009899
PCT Pub. Date: Feb. 2, 2023

(65) Prior Publication Data
US 2024/0260608 A1    Aug. 8, 2024

(30) Foreign Application Priority Data

Jul. 30, 2021 (AU) ................. 2021902354

(51) Int. Cl.
| | | |
|---|---|---|
| *A23K 10/16* | (2016.01) | |
| *A23K 20/189* | (2016.01) | |
| *A23K 50/10* | (2016.01) | |
| *A61K 36/062* | (2006.01) | |
| *A61K 38/44* | (2006.01) | |
| *C12N 1/14* | (2006.01) | |
| *C12N 9/08* | (2006.01) | |
| *C12R 1/645* | (2006.01) | |

(52) U.S. Cl.
CPC ............ *A23K 10/16* (2016.05); *A23K 20/189* (2016.05); *A23K 50/10* (2016.05); *A61K 36/062* (2013.01); *A61K 38/44* (2013.01); *C12N 1/145* (2021.05); *C12N 9/0065* (2013.01); *C12Y 111/01018* (2013.01); *C12R 2001/645* (2021.05)

(58) Field of Classification Search
CPC ........ A23K 10/16; A23K 10/18; A23K 50/10; A61K 38/44; C12Y 111/01018; C12N 1/145
See application file for complete search history.

(56) References Cited

U.S. PATENT DOCUMENTS

| | | | |
|---|---|---|---|
| 9,872,892 B2 * | 1/2018 | Klausen | A23K 20/189 |
| 2016/0051636 A1 * | 2/2016 | Klausen | A61K 38/44 424/94.4 |
| 2017/0196922 A1 | 7/2017 | Embree et al. | |

FOREIGN PATENT DOCUMENTS

| | | |
|---|---|---|
| AU | 2021105299 A4 | 10/2021 |
| CN | 106978355 A | 7/2017 |
| JP | 2005110573 A | 4/2005 |
| WO | 99/47651 | 9/1999 |
| WO | 2001/053494 A2 | 7/2001 |
| WO | 2011117552 A1 | 9/2011 |
| WO | 2014180953 A1 | 11/2014 |
| WO | 2015110663 A1 | 7/2015 |
| WO | 2017120495 A1 | 7/2017 |
| WO | 2019102279 A1 | 5/2019 |
| WO | 2020243792 A1 | 10/2020 |
| WO | 2022/266723 | 6/2022 |

OTHER PUBLICATIONS

Baumgartner et al. 2021 (Investigating the role of vanadium-dependent haloperoxidase enzymology in microbial secondary metabolism and chemical ecology; mSystems 6(4): 1-5) (Year: 2021).*
International Search Report and Written Opinion of the International Searching Authority for International Patent Application No. PCT/US2022/039095, 17 pages.
Baumgartner, J. T., & McKinnie, S. M. (2021). Investigating the role of vanadium-dependent haloperoxidase enzymology in microbial secondary metabolism and chemical ecology. Msystems, 6(4), 10-1128.

* cited by examiner

Primary Examiner — Mary Maille Lyons
(74) Attorney, Agent, or Firm — Adam Lunceford

(57) ABSTRACT

The present disclosure provides methods for reducing methane emissions from a ruminant comprising administering to the ruminant a composition comprising a fungal strain, wherein the fungal strain comprises a vanadium-dependent haloperoxidase (VHPO) such as *Curvularia* sp. strain 4388 (NMI Accession No. V22/011149). The disclosure also provides a cell or a biologically pure culture of *Curvularia* sp. strain 4388 (NMI Accession No. V22/011149) or a mutant thereof having all identifying characteristics of the strain.

5 Claims, 13 Drawing Sheets
Specification includes a Sequence Listing.

FIG. 5

```
1VNC    MGSVTPIPLPKIDEPEEYMTHYILFWWHVGLELNRVTHTVGGPLTGPPLSARALGMLHLA  60
4388    MGSITPIPLPKIDEPEEYMTHYILFWWHVGLELNRVTHTVGGPLTGPPLSARALGMLHLA  60
        ***:********************************************************

1VNC    IHDAYFSICPPTDFTTFLSPDTEMAAYRLPSPMGANDARQAVAGAALKMLSSLYMKPVEQ  120
4388    IHDAYFSIYPPTDFSTFLSPNAEMAAYRLPSPMGANDARQAVAGAALKMLTSLYMKPVET  120
        ********:*****:*****::*************************** *********

1VNC    PMPMPGAMISDMAYAQLGLVLDRSVLEAPGGVDRESASFMFGEDVADVFFALLMDPRGAS  180
4388    PMPMPGAMISDMAYAQLALVIDRSVLKAPGGVDRESASFMFGETVADVFFALLMDPRGAS  180
        *****************  **:*****.****************:***************

1VNC    QEGYHPTPGRYKFDDEPTHPVVLIPVDPMMPMGPKMPFRQYHAPFYGKTTKRFATQSEHF  240
4388    QEGYHPTPGRYKFDDEPTHPVVLIPVDPMMPMGPKKPFRQYHAPFYGKTTKRFATQSEHF  240
        ********************************** *************************

1VNC    LADPPGLRSMADETAEYDDAVRVAIAMGGAQALNSTKRSPMQTAQGLYMAYDGSMLIGTP  300
4388    LADPPGLRSMADETAEYDDAIRVAIAMGGAQALNSTKRSPMQTAQGLFMAYDGSMLIGTP  300
        ********************:*************************:*************

1VNC    PRFYNQIVRRIAVTYKKEEDLANSEVMMADFARLFALVDVACTDAGIFSWKEKWEFEFWR  360
4388    PRFYNQIVRRIAVTYKKEEDLANSEVMMADFARLFALVDVACTDAGIFSWKEKWEYEFWR  360
        ******************************************************:****

1VNC    PLSGVRDDGRPDHGDPFWLTLGAPATNTNDIPFKPPFPAYPSGHATFGGAVFQMVRRYYI  420
4388    PLSGVRDDGRPDHGDPFWLTLGAPATNTNDIPFKPPFPAYPSGHATFGGAVFQMVRRYYI  420
        ************************************************************

1VNC    GRVGTWKDDEPDMIAIDMMISEELMGVMRDLRQPYDPTAPIEDQPGIVRTRIVRHFDSAW  480
4388    GRVGTWKDDEPDMIAIDMMISEELMGLNRDLRQPYDPTAPIEDQPGIVRTRIVRHFDSAW  480
        **************************:*********************************

1VNC    ELMFENAISRIFLGVHWRFDAAAARDILIPTTTKDVYAVDNMGATVFQMVEDIRYTTRGT  540
4388    ELMFENAISRIFLGVHWRFDAAAARDILIPTTTKDVYAVDNMGATVFQMVEDIRYTTKGT  540
        ********************************************************:**

1VNC    REDEEGLFPIGGVPLGIEIADEIFMMGLKPTPPEIQPMPQETPVQKPVGQQPVKGMWEEE  600
4388    REDREGLFPIGGVPLGIEIADEIFMMGLKPTPPELQPMPQQTPVQKPVGQQPVQGMWAEE  600
        ***.*****************************:*****:************:***.**

1VNC    QAPVVKEAP    609
4388    QAPVIKEAP    609
        ****:****
```

FIG. 6

```
         ↓
4388  MGSITPIPLPKIDEPEEYNTNYILFWNHVGLELNRVTHTVGGPLTGPPLSARALGMLHLA  60
1VNC  MGSVTPIPLPKIDEPEEYNTNYILFWNHVGLELNRVTHTVGGPLTGPPLSARALGMLHLA  60
  28  MGSVTPIPLPKIDEPEEYNTNYILFWNHVGLELNRVTHTVGGPLTGPPLSARALGMLHLA  60
      ***:********************************************************

↓   ↓    ↓                              ↓
4388  IHDAYFSIYPPTDFSTFLSPNAENAAYRLPSPNGANDARQAVAGAALKMLTSLYMKPVET  120
1VNC  IHDAYFSICPPTDFTTFLSPDTENAAYRLPSPNGANDARQAVAGAALKMLSSLYMKPVEQ  120
  28  IHDAYFSICPPTDFTTFLSPDAENAAYRLPSPNGANDARQAVAGAALKMLSSLYMKPIEQ  120
      ******** ***** :****:  ***************************:******:*

↓↓  ↓
4388  PNPNPGANISDNAYAQLALVIDRSVLKAPGGVDRESASFMFGETVADVFFALLNDPRGAS  180
1VNC  PNPNPGANISDNAYAQLGLVLDRSVLEAPGGVDRESASFMFGEDVADVFFALLNDPRGAS  180
  28  PNPNPGANISDNAYAQLGLVLDRSVLEAPGGVDRESASFMFGEAVADVFFALLNDPRGAS  180
      *****************.**:*****:***************  ****************

4388  QEGYHPTPGRYKFDDEPTHPVVLIPVDPNNPNGPKKPFRQYHAPFYGKTTKRFATQSEHF  240
1VNC  QEGYHPTPGRYKFDDEPTHPVVLIPVDPNNPNGPKMPFRQYHAPFYGKTTKRFATQSEHF  240
  28  QEGYHPTPGRYKFDDEPTHPVVLIPVDPNNPNGPKKPFRQYHAPFYGKTTKRFATQSEHF  240
      *********************************** ************************

↓
4388  LADPPGLRSNADETAEYDDAIRVAIAMGGAQALNSTKRSPWQTAQGLFWAYDGSNLIGTP  300
1VNC  LADPPGLRSNADETAEYDDAVRVAIAMGGAQALNSTKRSPWQTAQGLYWAYDGSNLIGTP  300
  28  LADPPGLRSNADETAEYDDAIRVAIAMGGAQALNSTKRSPWQTAQGLYWAYDGSNLIGTP  300
      ********************:**************************:************

↓
4388  PRFYNQIVRRIAVTYKKEEDLANSEVNNADFARLFALVDVACTDAGIFSWKEKWEYEFWR  360
1VNC  PRFYNQIVRRIAVTYKKEEDLANSEVNNADFARLFALVDVACTDAGIFSWKEKWEFEFWR  360
  28  PRFYNQIVRRIAVTYKKEEDLANSEVNNADFARLFALVDVACTDAGIFSWKEKWEFEFWR  360
      ******************************************************:****

4388  PLSGVRDDGRPDHGDPFWLTLGAPATNTNDIPFKPPFPAYPSGHATFGGAVFQMVRRYYN  420
1VNC  PLSGVRDDGRPDHGDPFWLTLGAPATNTNDIPFKPPFPAYPSGHATFGGAVFQMVRRYYN  420
  28  PLSGVRDDGRPDHGDPFWLTLGAPATNTNDIPFKPPFPAYPSGHATFGGAVFQMVRRYYN  420
      ************************************************************

4388  GRVGTWKDDEPDNIAIDMMISEELNGLNRDLRQPYDPTAPIEDQPGIVRTRIVRHFDSAW  480
1VNC  GRVGTWKDDEPDNIAIDMMISEELNGVNRDLRQPYDPTAPIEDQPGIVRTRIVRHFDSAW  480
  28  GRVGTWKDDEPDNIAIDMMISEELNGLNRDLRQPYDPTAPIEDQPGIVRTRIVRHFDSAW  480
      **************************:*********************************

4388  ELMFENAISRIFLGVHWRFDAAAARDILIPTTTKDVYAVDNNGATVFQNVEDIRYTTKGT  540
1VNC  ELMFENAISRIFLGVHWRFDAAAARDILIPTTTKDVYAVDNNGATVFQNVEDIRYTTRGT  540
  28  ELMFENAISRIFLGVHWRFDAAAARDILIPTTTKDVYAVDNNGATVFQNVEDIRYTTKGT  540
      ********************************************************:**

↓      ↓      ↓ ↓
4388  REDREGLFPIGGVPLGIEIADEIFNNGLKPTPPELQPMPQQTPVQKPVGQQPVQGMWAEE  600
1VNC  REDEEGLFPIGGVPLGIEIADEIFNNGLKPTPPEIQPMPQETPVQKPVGQQPVKGMWEEE  600
  28  REDREGLFPIGGVPLGIEIANEIFNNGLKPTPPEIQPMPQETPVQE-----PVKGMWEEE  595
      ***.****************:*************:*****:****:     **:*** **

4388  QAPVIKEAP  609
1VNC  QAPVVKEAP  609
  28  QAPIIKEAP  604
      ***::****
```

METHODS FOR THE REDUCTION OF METHANE PRODUCTION IN RUMINANTS

CROSS REFERENCE TO RELATED APPLICATIONS

This application is the U.S. National Stage of International Application No. PCT/US2022/039095, filed on Aug. 2, 2022, which claims the benefit of Australian Provisional Patent Application No. 2021902354, filed on Jul. 30, 2021, the contents of which are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled LOAM-B001WO_Sequence_Listing.txt, 18,524 bytes in size, generated on Aug. 1, 2022, and filed via EFS-Web, is provided in lieu of a paper copy. This Sequence Listing is incorporated by reference into the specification for its disclosures.

TECHNICAL FIELD

The present disclosure relates to the reduction of methane emissions from ruminants. Specifically, the present invention relates to methods and processes associated with the use of fungal strains that, when administered to ruminants, can reduced the methane production of methanogens in the rumen, thereby reducing methane emissions.

BACKGROUND

Marine macroalgae, seaweeds, are producers of halogenated natural products. Biosynthesis of halogenated molecules is linked to reactive oxygen species (ROS) such as hydrogen peroxide that are substrates for haloperoxidase enzymes that promote the formation of halogenated molecules (23). It has been shown that vanadium-dependent haloperoxidases (VHPOs), halogenating enzymes that are present in seaweeds, are involved in bromoform biosynthesis. The importance of bromoform synthesis is that it can inhibit methane production (23-24). The antimethanogenic activity of bromoform was studied in vitro by isolating bioactive compound from the red seaweed *Asparagopsis taxiformis*.

The red macroalga *Asparagopsis taxiformis* has been linked to the reduction of methane ($CH_4$) from beef cattle by up to 99% (25). A recent study shows that *A. taxiformis* is a highly efficient feed supplement for $CH_4$ mitigation during enteric fermentation (24). The antimethanogenic compounds found in *A. taxiformis* are: bromoform, dibromochloromethane, bromochloroacetic acid, dibromoacetic acid and dichloromethane. However, bromoform, a halomethane, is the most abundant antimethanogenic compound found in *A. taxiformis* (26). On the other hand, bromoform and dibromochloromethane had the highest activity at inhibiting methane production (26).

Bromoform is a halogen that has been found to interfere with the methanogenesis pathway by serving as a competitive inhibitor or analog of methyl-coenzyme M reductase (MCR), preventing the final catalysis step (27-28).

It would be attractive, practically and commercially, to be able to reduce the methane emissions produced by ruminants, and in particular, domestic livestock, by using a source of bromoform that is easily produced with limited impact on the environment. Fungal strains expressing VHPOs present an alternative to marine macroalgae for accomplishing this objective.

SUMMARY

To overcome limitations in the prior art described above, and to overcome other limitations that will be apparent upon reading and understanding the present specification, aspects described herein are directed towards systems, apparatuses, computer-readable media, memory, and methods for An aspect of the present disclosure provides a method for reducing the methane emissions of a ruminant comprising administering to said ruminant a composition comprising a fungal biomass, wherein said fungal biomass comprises at least one fungal strain capable of producing bromoform.

In embodiments of the invention, the fungal strain is one that comprises one or more vanadium-dependent haloperoxidases (VHPO) genes.

In some embodiments, the disclosure provides a method for reducing methane emissions from a ruminant comprising administering to the ruminant a composition comprising a fungal strain, biomass from the fungal strain, a culture supernatant from the fungal strain, or a combination thereof, wherein the fungal strain comprises a vanadium-dependent haloperoxidase (VHPO) with an amino sequence having at least 80% identity with SEQ ID NO: 2.

In one aspect, biomass from the fungal strain is administered to the ruminant. In another aspect, a culture supernatant from the fungal strain is administered to the ruminant. In another aspect, a whole broth from the fungal strain is administered to the ruminant.

In some embodiments, the amino acid sequence of the VHPO comprises an isoleucine at position 3, a tyrosine at position 69, a serine at position 75, an asparagine at position 81, an alanine at position 82, a threonine at position 111, a threonine at position 120, an alanine at position 138, an isoleucine at position 141, a lysine at position 147, a threonine at position 163, a lysine at position 215, an isoleucine at position 261, a phenylalanine at position 288, a tyrosine at position 356, a leucine at position 447, a lysine at position 538, an arginine at position 544, a leucine at position 575, a glutamine at position 581, a glutamine at position 594, an alanine at position 598, an isoleucine at position 605, or a combination thereof.

In one embodiment, the amino acid sequence of the VHPO comprises a tyrosine at position 69, a phenylalanine at position 288, and a tyrosine at position 356. In one aspect, bromination of surface exposed aromatic residues promotes haloperoxidase activity of the VHPO.

In some aspects, the amino acid sequence of the VHPO comprises a tyrosine at position 69, a threonine at position 120, a threonine at position 163, and a glutamine at position 581.

In one aspect, the amino acid sequence of the VHPO comprises an isoleucine at position 3, a tyrosine at position 69, a serine at position 75, an asparagine at position 81, a threonine at position 111, an alanine at position 138, an isoleucine at position 141, a lysine at position 147, a phenylalanine at position 288, a tyrosine at position 356, a leucine at position 575, a glutamine at position 581, a glutamine at position 594, and an alanine at position 598.

In another aspect, the amino acid sequence of the VHPO comprises an isoleucine at position 3, a tyrosine at position 69, a serine at position 75, an asparagine at position 81, an alanine at position 82, a threonine at position 111, a threonine at position 120, an alanine at position 138, an isoleucine at position 141, a lysine at position 147, a threonine at position 163, a lysine at position 215, an isoleucine at position 261, a phenylalanine at position 288, a tyrosine at position 356, a leucine at position 447, a lysine at position 538, an arginine at position 544, a leucine at position 575, a glutamine at position 581, a glutamine at position 594, an alanine at position 598, and an isoleucine at position 605.

In other aspects, the amino acid sequence of the VHPO further comprises an arginine at position 360, a serine at position 402, a histidine at position 404, an arginine at position 490, and a histidine at position 496.

In certain embodiments, the VHPO forms a dimer and a flexible loop at the carboxy terminal region of the VHPO modulates haloperoxidase activity by modifying solvation rate and interaction with bromide (Br) species.

In other embodiments, the fungal strain belongs to the genus *Curvularia*.

In other aspects, the disclosure provides a method for reducing methane emissions from a ruminant comprising administering to the ruminant a composition comprising a fungal strain, biomass from the fungal strain, a culture supernatant from the fungal strain, or a combination thereof, wherein the fungal strain is *Curvularia* sp. strain 4388 (NMI Accession No. V22/011149) or a mutant thereof having all identifying characteristics of the strain. In some aspects, the identifying characteristics include similar VHPO activity (e.g., at least 60%, at least 70%, at least 80%, or at least 90% of that observed with *Curvularia* sp. strain 4388).

In some aspects, the ruminant is a member of the family Bovidae. In one aspect, the ruminant is *Bos taurus*.

In other embodiments, the disclosure provides a cell or a biologically pure culture of a fungal strain comprising a VHPO with an amino sequence having at least 80% identity with SEQ ID NO: 2.

In some embodiments, the disclosure provides a cell or a biologically pure culture of *Curvularia* sp. strain 4388 (NMI Accession No. V22/011149) or a mutant thereof having all identifying characteristics of the strain.

In other aspects, the disclosure provides an agricultural composition comprising a cell or a biologically pure culture as disclosed herein or biomass from the cell or biologically pure culture, a culture supernatant from the cell or biologically pure culture, or a combination thereof, and, optionally, an agriculturally acceptable carrier. In some aspects, the agricultural composition further comprises a cereal, starch, vegetable waste, vitamin, mineral, trace element, emulsifier, aromatizing product, binder, colorant, odorant, thickening agent, or a combination thereof.

In other aspects, the disclosure provides a use of a cell or a biologically pure culture or an agriculture composition as disclosed herein for reducing methane emissions from a ruminant.

In some aspects, the disclosure provides a method of increasing expression of VHPO in a fungal strain, the method comprising culturing the fungal strain in a culture medium comprising at least 1 g/L, 2 g/L, 3 g/L, 4 g/L, or 5 g/L glucose. In one aspect, the culture medium comprises at least 5 g/L glucose. In another aspect, the fungal strain belongs to the genus *Curvularia*. In another aspect, the fungal strain is *Curvularia* sp. strain 4388 (NMI Accession No. V22/011149) or a mutant thereof having all identifying characteristics of the strain.

Other and further aspects and features of the disclosure will be evident from reading the following detailed description of the embodiments, which are intended to illustrate, not limit, the present disclosure.

BRIEF DESCRIPTION OF THE DRAWINGS

FIG. 5 depicts a Clustal Omega Alignment of *Curvularia* sp. strain 4388 VHPO (SEQ ID NO: 2; "4388") and *Curvularia inaequalis* PDB ID 1VNC VHPO (SEQ ID NO: 3; "1VNC").

Amino acid differences are marked with black arrows.

FIG. 6 depicts a Clustal Omega Alignment of *Curvularia* sp. strain 4388 VHPO (SEQ ID NO: 2; "4388"), *Curvularia inaequalis* PDB ID 1VNC VHPO (SEQ ID NO: 3; "1VNC"), and *Curvularia inaequalis* strain 28 VHPO (SEQ ID NO: 4; "28"). Amino acid differences common with those indicated in FIG. 5 are marked with black arrows.

Figure 7:
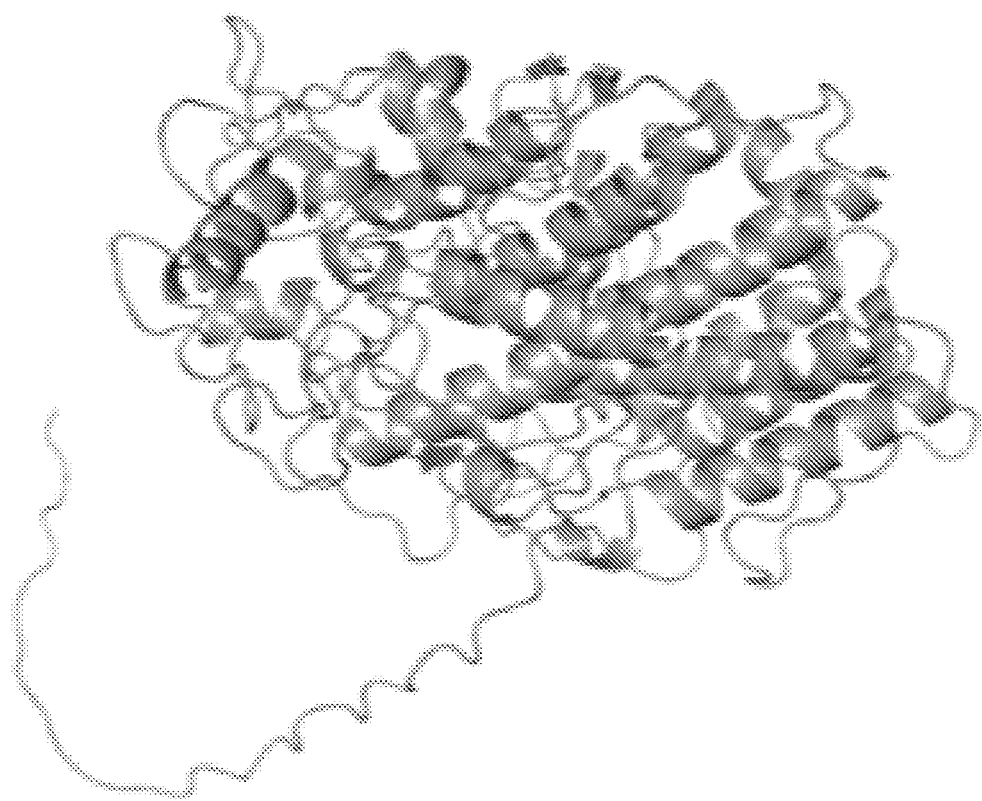

FIG. 7 depicts a three-dimensional structure of the *Curvularia* sp. strain 4388 VHPO protein.

Figure 8C:
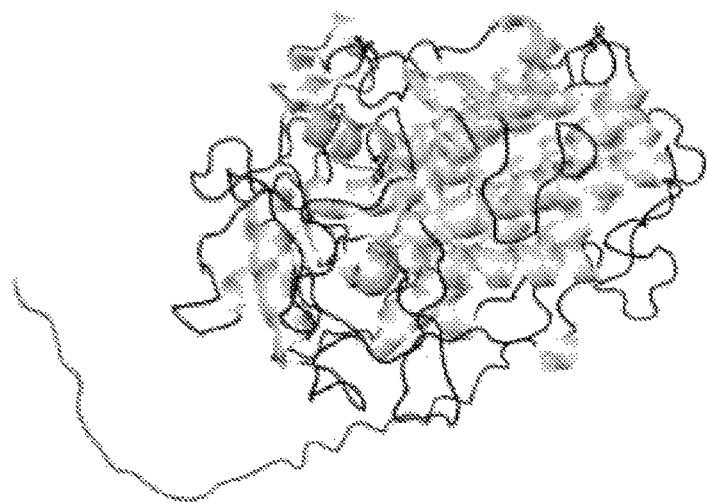
Figure 8B:
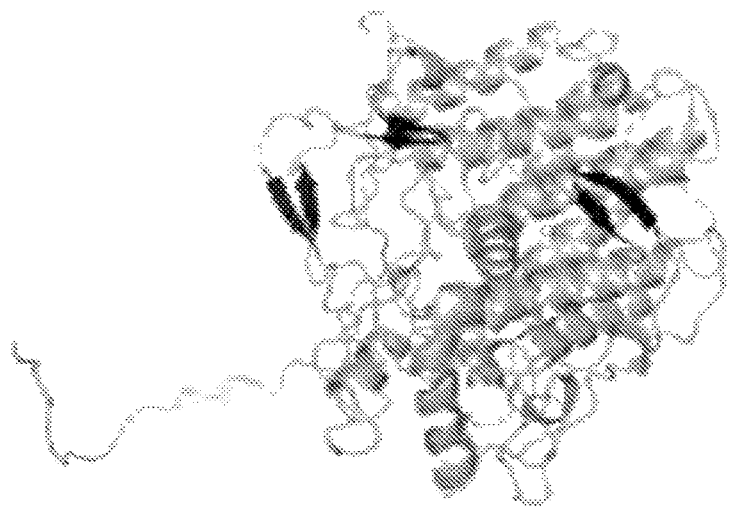
Figure 8A:
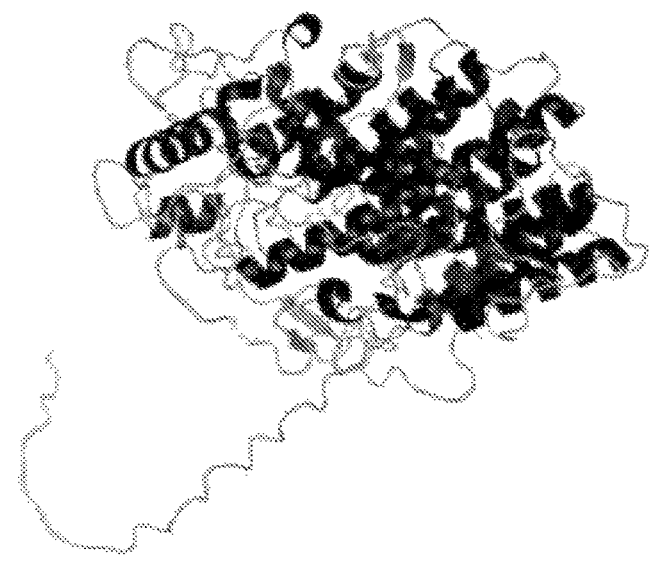

FIGS. 8A, 8B, and 8C depict the three-dimensional structure of the *Curvularia* sp. strain 4388 VHPO protein with alpha helices shown in black, β-structures shown in black, and loops shown in black, respectively.

Figure 9:
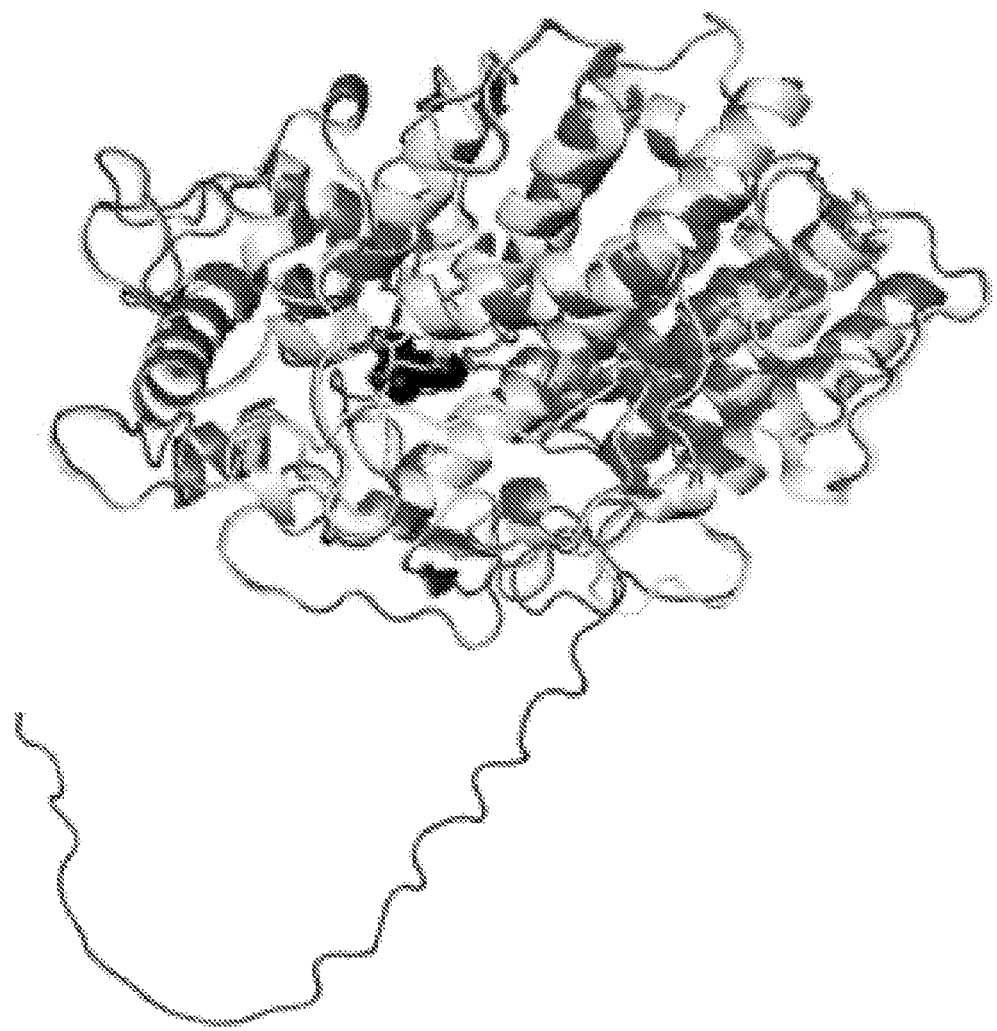

FIG. 9 depicts the overlap of *Curvularia* sp. strain 4388 VHPO and *Curvularia inaequalis* PDB ID 1VNC VHPO. Dark black regions represent *Curvularia* sp. strain 4388 VHPO, and light gray regions represent *Curvularia inaequalis* PDB ID 1VNC VHPO.

Figure 10:
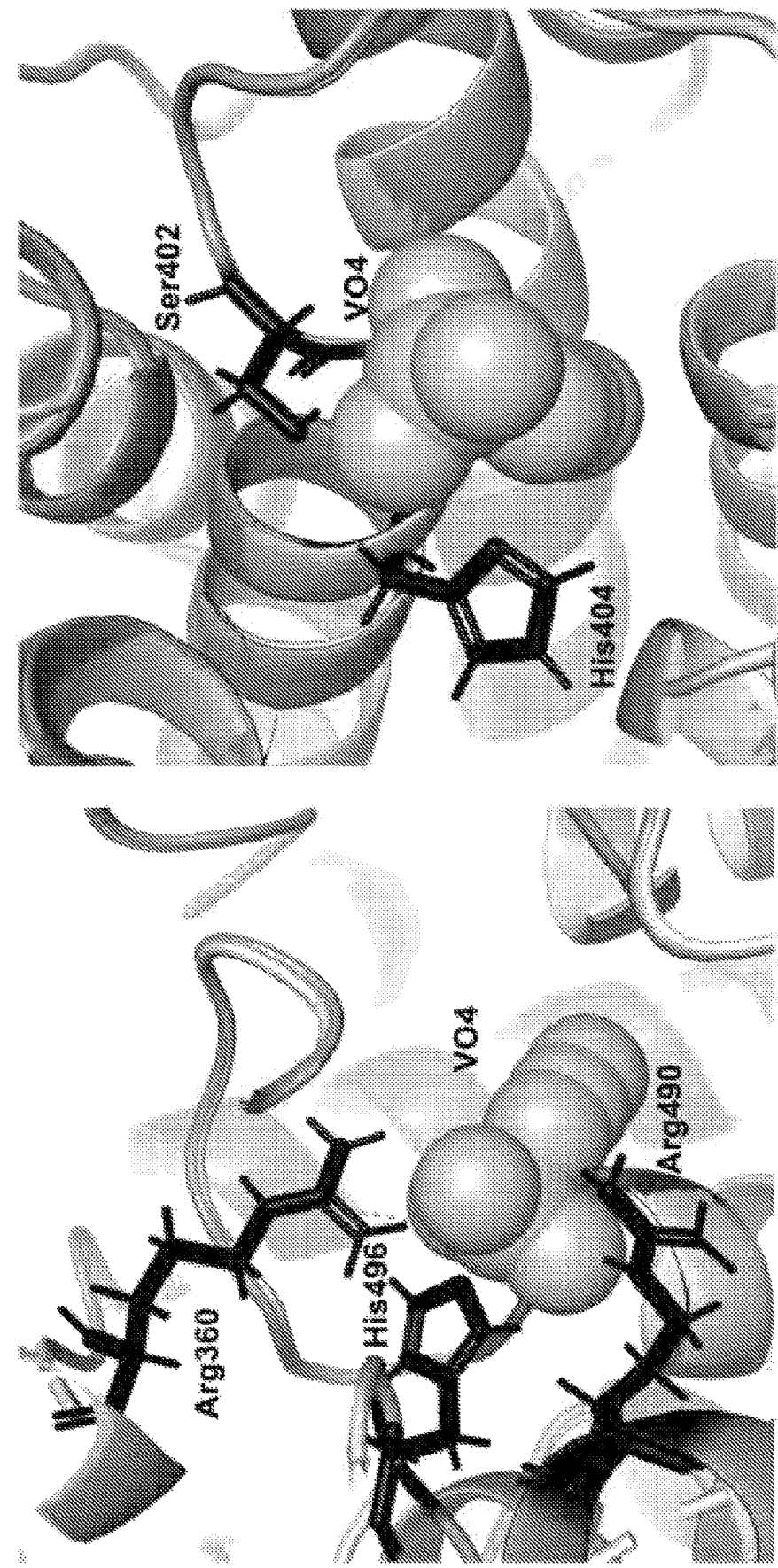

FIG. 10 depicts the vanadate coordination site in *Curvularia* sp. strain 4388 VHPO.

Figure 11:
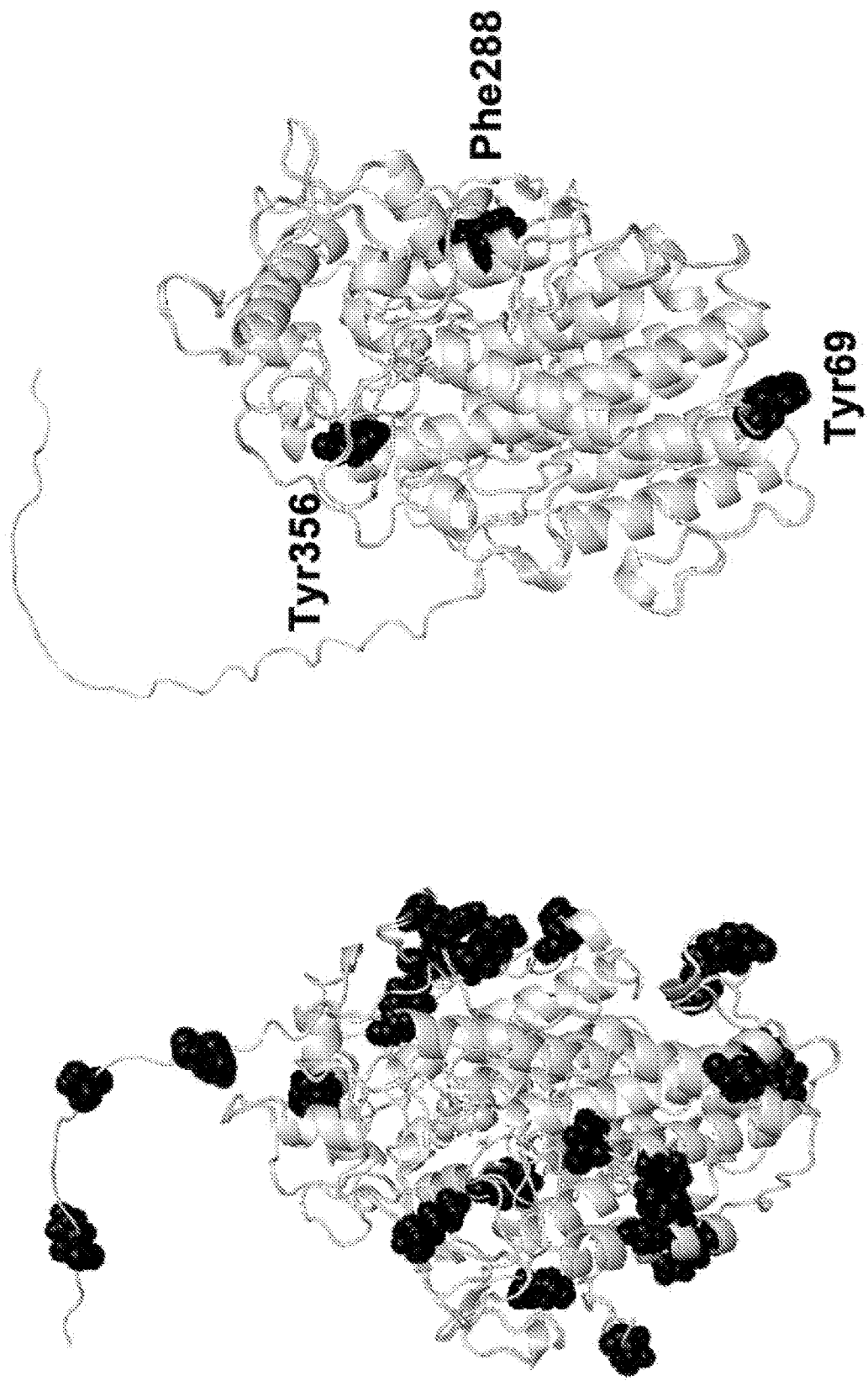

FIG. 11 depicts 23 amino acid variations in *Curvularia* sp. strain 4388 VHPO compared to *Curvularia inaequalis* PDB ID 1VNC VHPO (left structure) among which are three surface exposed tyrosine/phenylalanine substitutions (right structure).

Figure 12:
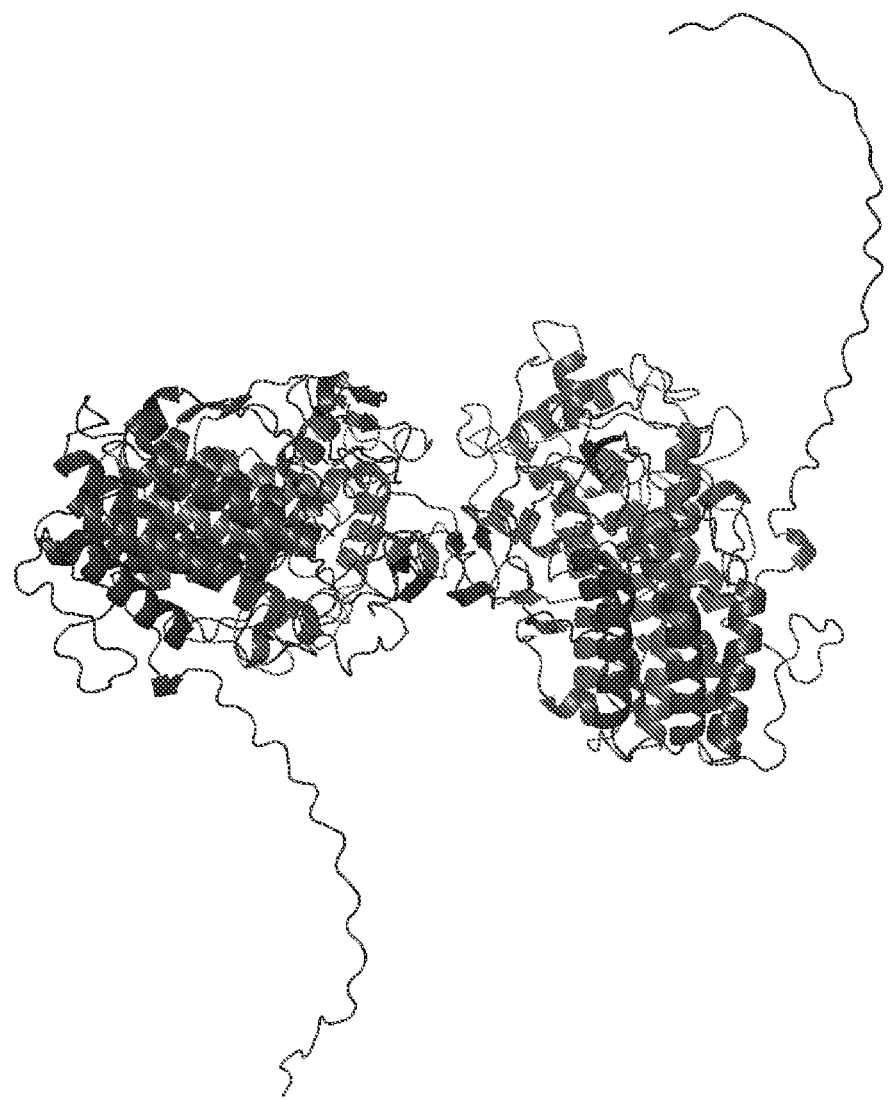

FIG. 12 depicts dimerization of *Curvularia* sp. strain 4388 VHPO that increases stability and haloperoxidase activity.

Figure 13:
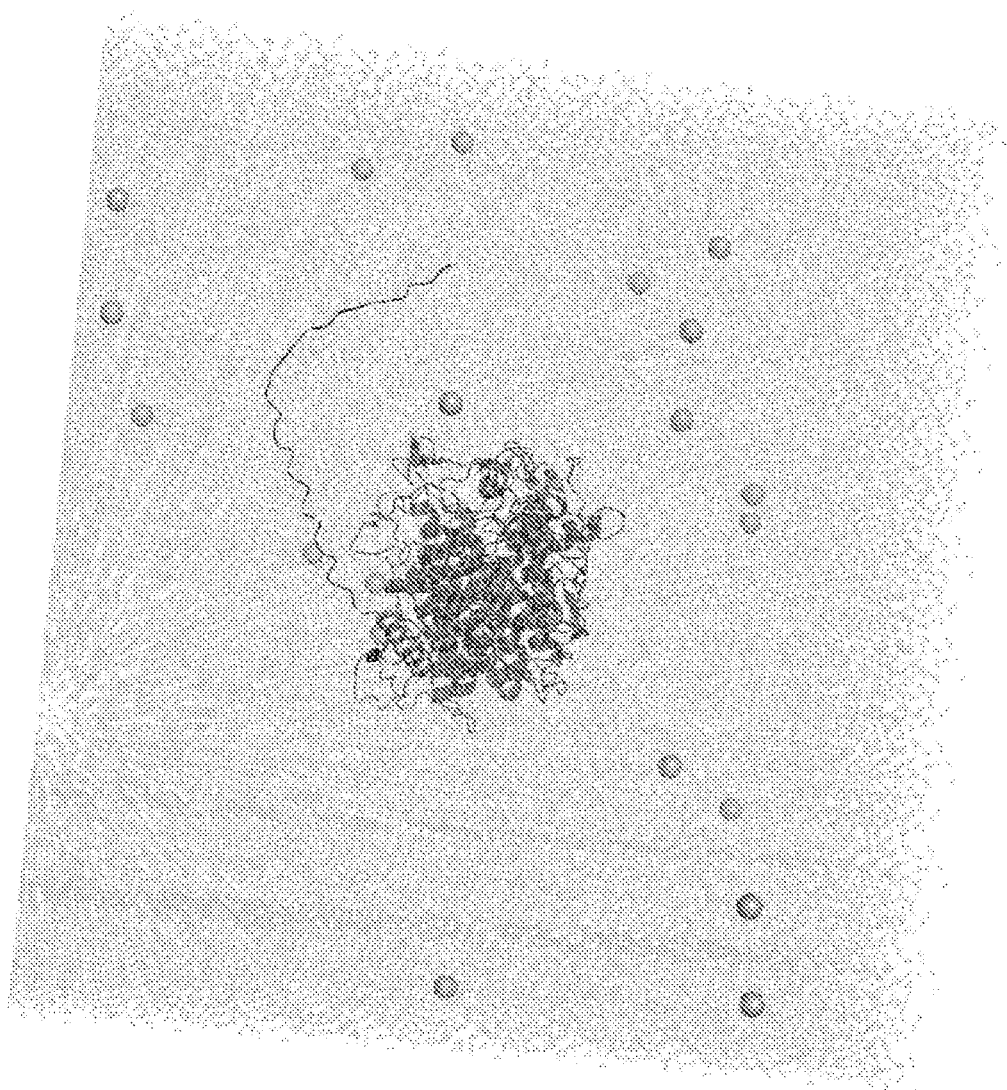

FIG. 13 depicts the solvent accessible area of *Curvularia* sp. strain 4388 VHPO and energy minimized conformation. The presence of a flexible loop at the carboxy terminal modulates haloperoxidase activity.

The following description is intended only by way of example, and simply illustrates certain selected embodiments of devices, systems, and processes that are consistent with the disclosed subject matter as claimed herein.

DETAILED DESCRIPTION

Preferred features, embodiments and variations of the invention may be discerned from the following detailed description which provides sufficient information for those skilled in the art to perform the invention. The detailed description is not to be regarded as limiting the scope of the preceding summary of the invention in any way.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

As used herein, the term "ruminant" includes mammals that are capable of acquiring nutrients from plant-based food by fermenting it in a specialized stomach (rumen) prior to digestion, principally through microbial actions. Ruminants included cattle, goats, sheep, giraffes, yaks, deer, antelope, and others.

As used herein, the term "bovid" includes any member of the family Bovidae, which include hoofed mammals such as antelope, sheep, goats, and cattle, among others.

As used herein, the term "reducing" includes the reduction of amount of substance in comparison with a reference. For example, the reduction in the amount of total gas and/or methane produced by a ruminant animal or animals administered a composition comprising a fungal strain according to the present invention, relative to an animal or animals not administered a composition comprising a fungal strain of the present invention. The reduction can be measured in vitro with an artificial rumen system that simulates anaerobic fermentation, or in vivo with animals confined in respiration chambers. It is within the knowledge and skill of those trained in the art to assess enteric methanogenesis by a ruminant animal.

As used herein, the term "reducing methane production" refers to the reduction of methane produced in the gastro-intestinal tract. The term includes the specific volume of methane generated as a result of anaerobic fermentation, for example, in the systems described herein. Fermentation in the rumen and the gut of a ruminant gives rise to production of methane. The present invention aims to reduce this process, such as to reduce the total amount of methane produced in the gastro-intestinal tract. It is within the knowledge and skill of those trained in the art to assess methane production by a ruminant animal.

A "ruminant" is a mammal of the order Artiodactyla that digests plant-based food by initially softening and partially fermenting it within the animal's first stomach chambers, then regurgitating the semi-digested mass, now known as cud, and chewing it again. The process of rechewing the cud to further break down plant matter and stimulate digestion is called "ruminating". Ruminants have a digestive tract with four chambers, namely the rumen, reticulum, omasum and abomasum. In the first two chambers, the rumen and the reticulum, the food is mixed with saliva and separates into layers of solid and liquid material. Solids clump together to form the cud, or bolus. The cud is then regurgitated, chewed slowly to completely mix it with saliva, which further breaks down fibers. Fiber, especially cellulose, is broken down into glucose in these chambers by symbiotic anaerobic bacteria, protozoa and fungi. The broken-down fiber, which is now in the liquid part of the contents, then passes through the rumen into the next stomach chamber, the omasum. The food in the abomasum is digested much like it would be in the monogastric stomach. Digested gut contents are finally sent to the small intestine, where the absorption of the nutrients occurs. Almost all the glucose produced by the breaking down of cellulose is used by the symbiotic bacteria. Ruminants get their energy from the volatile short chain fatty acids (VFAs) produced by the bacteria, namely acetate, propionate, butyrate, valerate, and isovalerate.

Fungal Strains Expressing a Vanadium-Dependent Haloperoxidase

In certain aspects, the present disclosure provides a method for reducing methane emissions from a ruminant comprising administering to the ruminant a composition comprising a fungal strain, biomass from the fungal strain, a culture supernatant from the fungal strain, or a combination thereof, wherein the fungal strain comprises a vanadium-dependent haloperoxidase (VHPO).

In some aspects, the amino acid sequence of the VHPO comprises an amino sequence having at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with SEQ ID NO: 2. In one aspect, the VHPO comprises or consists of SEQ ID NO: 2.

In other aspects, the VHPO is a variant protein of the protein comprising or consisting of the amino acid sequence of SEQ ID NO: 2. Variants proteins are within the scope of the invention as long as the resulting variant protein retains similar characteristics when compared to the parent peptide. Exemplary modifications are for example conservative substitutions that will result in VHPO variants with similar characteristics to those of the parent molecules. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Non-conservative substitutions can be made to the VHPO variants that involve substitutions of amino acid residues between different classes of amino acids to improve properties of the VHPO variants. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement takes place can readily be tested in the same manner.

The following conservative substitutions can be made in a VHPO from a fungal strain with the positions corresponding to those in SEQ ID NO: 2.

In certain aspects, the VHPO amino acid sequence comprises an aliphatic residue at position 3. In one aspect, the aliphatic residue at position 3 is isoleucine.

In certain aspects, the VHPO amino acid sequence comprises an aromatic residue at position 69. In one aspect, the aromatic residue at position 69 is tyrosine.

In certain aspects, the VHPO amino acid sequence comprises an aliphatic residue at position 75. In one aspect, the aliphatic residue at position 75 is serine.

In certain aspects, the VHPO amino acid sequence comprises an amide residue at position 81. In one aspect, the amide residue at position 81 is asparagine.

In certain aspects, the VHPO amino acid sequence comprises an aliphatic residue at position 82. In one aspect, the aliphatic residue at position 82 alanine.

In certain aspects, the VHPO amino acid sequence comprises an aliphatic residue at position 111. In one aspect, the aliphatic residue at position 111 is threonine.

In certain aspects, the VHPO amino acid sequence comprises an aliphatic residue at position 120. In one aspect, the aliphatic residue at position 120 is threonine.

In certain aspects, the VHPO amino acid sequence comprises an aliphatic residue at position 138. In one aspect, the aliphatic residue at position 138 is alanine.

In certain aspects, the VHPO amino acid sequence comprises an aliphatic residue at position 141. In one aspect, the aliphatic residue at position 141 is isoleucine.

In certain aspects, the VHPO amino acid sequence comprises a basic residue at position 147. In one aspect, the basic residue at position 147 is lysine.

In certain aspects, the VHPO amino acid sequence comprises an aliphatic residue at position 163. In one aspect, the aliphatic residue at position 163 is threonine.

In certain aspects, the VHPO amino acid sequence comprises a basic residue at position 215. In one aspect, the basic residue at position 215 is lysine.

In certain aspects, the VHPO amino acid sequence comprises an aliphatic residue at position 261. In one aspect, the aliphatic residue at position 261 is isoleucine.

In certain aspects, the VHPO amino acid sequence comprises an aromatic residue at position 288. In one aspect, the aromatic residue at position 288 is phenylalanine.

In certain aspects, the VHPO amino acid sequence comprises an aromatic residue at position 356. In one aspect, the aromatic residue at position 356 is tyrosine.

In certain aspects, the VHPO amino acid sequence comprises an aliphatic residue at position 447. In one aspect, the aliphatic residue at position 447 is leucine.

In certain aspects, the VHPO amino acid sequence comprises a basic residue at position 538. In one aspect, the basic residue at position 538 is lysine.

In certain aspects, the VHPO amino acid sequence comprises a basic residue at position 544. In one aspect, the basic residue at position 544 is arginine.

In certain aspects, the VHPO amino acid sequence comprises an aliphatic residue at position 575. In one aspect, the aliphatic residue at position 575 is leucine.

In certain aspects, the VHPO amino acid sequence comprises an amide residue at position 581. In one aspect, the amide residue at position 581 is glutamine.

In certain aspects, the VHPO amino acid sequence comprises an amide residue at position 594. In one aspect, the amide residue at position 594 is glutamine.

In certain aspects, the VHPO amino acid sequence comprises an aliphatic residue at position 598. In one aspect, the aliphatic residue at position 598 is alanine.

In certain aspects, the VHPO amino acid sequence comprises an aliphatic residue at position 605. In one aspect, the aliphatic residue at position 605 is isoleucine.

In certain aspects, the VHPO amino acid sequence comprises a basic residue at position 496. In one aspect, the basic residue at position 496 is histidine.

In certain aspects, the VHPO amino acid sequence comprises a basic residue at position 360. In one aspect, the basic residue at position 360 is arginine.

In certain aspects, the VHPO amino acid sequence comprises a basic residue at position 490. In one aspect, the basic residue at position 490 is arginine.

In certain aspects, the VHPO amino acid sequence comprises an aliphatic residue at position 402. In one aspect, the aliphatic residue at position 402 is serine.

In certain aspects, the VHPO amino acid sequence comprises a basic residue at position 404. In one aspect, the basic residue at position 404 is histidine.

Animal Feed

Also disclosed herein is an animal feed comprising the compositions described herein (i.e., a composition comprising a fungal strain, biomass from the fungal strain, a culture supernatant from the fungal strain, or a combination thereof). The animal feed may be solid (e.g. powder, granules, pellets), semi-solid (e.g. gel, ointment, cream, paste) or liquid (e.g. solutions, suspensions, emulsions). The animal feed may independently be solid, semi-solid (e.g. gel, ointment, cream, paste) or liquid (e.g. solutions, suspensions, emulsions). For example, the animal feed may both be liquid or both be semi-solid or both be solid. Alternatively, the animal feed and composition may each be a different physical state. For example, the animal feed may be solid or semi-solid and the composition may be liquid. The composition may, for example, be used to "top-dress" (added on top) a ruminant feedlot ration or may be used to blend into a total mixed ration.

The composition may, for example, be added to the drinking water of the animal. In certain embodiments, the composition may be added to the drinking water of the animal immediately before ingestion, for example up to 1 hour before ingestion or up to 30 minutes before ingestion or up to 15 minutes before ingestion or up to 5 minutes before ingestion.

The three main types of animal feed include roughages, concentrates and mixed feeds. In general, roughages contain a higher percentage of crude fiber and a lower percentage of digestible nutrients than concentrates. For example, roughages may be defined as containing equal to or greater than 20 wt % crude fiber and equal to or less than 60 wt % total digestible nutrients. Roughages may include, for example, dry roughages (e.g. hay, straw, artificially dehydrated forages containing at least 90 wt % dry matter), silages (formed from green forages such as grass, alfalfa, sorghum and corn and preserved in a silo at dry matter contents of 20 to 50%), and pastures (e.g. green growing pastures providing forage that has a high water content and generally less than 30% dry matter). The two basic types of roughages include grasses and legumes. Grasses are generally higher in fiber and dry matter than legumes. Legumes are generally higher in proteins, metabolizable energy, vitamins and minerals. Concentrates contain a relatively lower percentage of crude fiber and a higher percentage of digestible nutrients than roughages. For example, concentrates may be defined as containing less than 20 wt % crude fiber and greater than 60 wt % total digestible nutrients. Concentrates may include, for example, energy-rich grains and molasses. Corn, wheat, oats, barley and milo (sorghum grain) are energy-rich grains, containing about 70 to 80 wt % total digestible nutrients.

Mixed feeds are generally a mixture of roughages and concentrates to provide "complete" balanced rations and may be either high or low in energy, protein or fiber. The disclosed compositions and fungal strains, for example, can be combined with animal feed in various amounts depending on the total amount of fungal strain, culture supernatant from the fungal strain, or combination thereof intended to be administered to the animal.

The animal feed may, for example, comprise from about 0.0001 wt % to about 10 wt % of disclosed compositions, based on the total dry weight of the animal feed. The animal feed may, for example, comprise from about 0.01 wt % to about 10 wt % of disclosed composition, based on the total dry weight of the animal feed. For example, the animal feed may comprise from about 0.001 wt % to about 9.5 wt %, or from about 0.005 wt % to about 9 wt %, or from about 0.01 wt % to about 8.5 wt %, or from about 0.05 wt % to about 8 wt %, or from about 0.1 wt % to about 7.5 wt %, or from about 0.9 wt % to about 7 wt %, or from about 1 wt % to about 6 wt %, or from about 1.5 wt % to about 5.5 wt %, or from about 2 wt % to about 5 wt %, or from about 2.5 wt % to about 4.5 wt %, or from about 3 wt % to about 4 wt % disclosed composition based on the total dry weight of the animal feed. For example, the animal feed may comprise from about 0.4 wt % to about 9.5 wt %, or from about 0.5 wt % to about 9 wt %, or from about 0.6 wt % to about 8.5 wt %, or from about 0.7 wt % to about 8 wt %, or from about 0.8 wt % to about 7.5 wt %, or from about 0.9 wt % to about 7 wt %, or from about 1 wt % to about 6 wt %, or from about 1.5 wt % to about 5.5 wt %, or from about 2 wt % to about 5 wt %, or from about 2.5 wt % to about 4.5 wt %, or from about 3 wt % to about 4 wt % disclosed composition based on the total dry weight of the animal feed.

In one embodiment, the fungal strain, biomass from the fungal strain, a culture supernatant from the fungal strain, or a combination thereof is administered at a dose of preferably at least 16.67, 10, 5, 3, 2, 1, 0.5, 0.25 0.125 or 0.067% of the organic matter administered to the ruminant animal. For example, if a 450 kg ruminant animal (e.g., steer) consumes 2.5% to 3% of its body weight per day of feed, then the fungal strain is administered at a dose proportional to the amount of organic matter administered to the ruminant. In the case of a 450 kg ruminant animal, and where 80% of the feed is organic matter, if the animal consumes about 2.5% of its body weight per day, then the fungal strain, biomass from the fungal strain, a culture supernatant from the fungal strain, or a combination thereof is administered at a dose of about 0.27, 0.18, 0.09, 0.045, 0.0225, 0.01125 or 0.00603 kg per day to result in a dose at least 3, 2, 1, 0.5, 0.25 0.125 or 0.067% of the organic matter administered to the ruminant animal.

Biological Deposit of *Curvularia* sp. Strain 4388

A Biological Deposit of *Curvularia* sp. strain 4388 was made at the National Measurement Institute (NMI), 1/153 Bertie Street, Port Melbourne, Victoria 3207, Australia, on 10 Jun. 2022 under the provisions of the Budapest Treaty, and assigned by the International Depositary Authority the accession number V22/011149. Upon issuance of a patent, all restrictions upon the Deposit will be irrevocably removed. The Deposit is intended to meet the requirements of 37 CFR §§ 1.801-1.809. The Deposit will be maintained in the depository for a period of 30 years, or 5 years after the last request, or for the effective, enforceable life of the patent, whichever is longer, and will be replaced, if necessary, during that period. The requirements of 37 CFR §§ 1.801-1.809 are met Any embodiment of the invention is meant to be illustrative only and is not meant to be limiting to the invention. Therefore, it should be appreciated that various other changes and modifications can be made to any embodiment described without departing from the spirit and scope of the invention.

All headings are for the convenience of the reader and should not be used to limit the meaning of the text that follows the heading, unless so specified.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Enhanced Vanadium-Dependent Haloperoxidase (VHPO) Activity in the Biomass and Supernatant Fractions from *Curvularia* sp. Strain 4388

Figure 1:
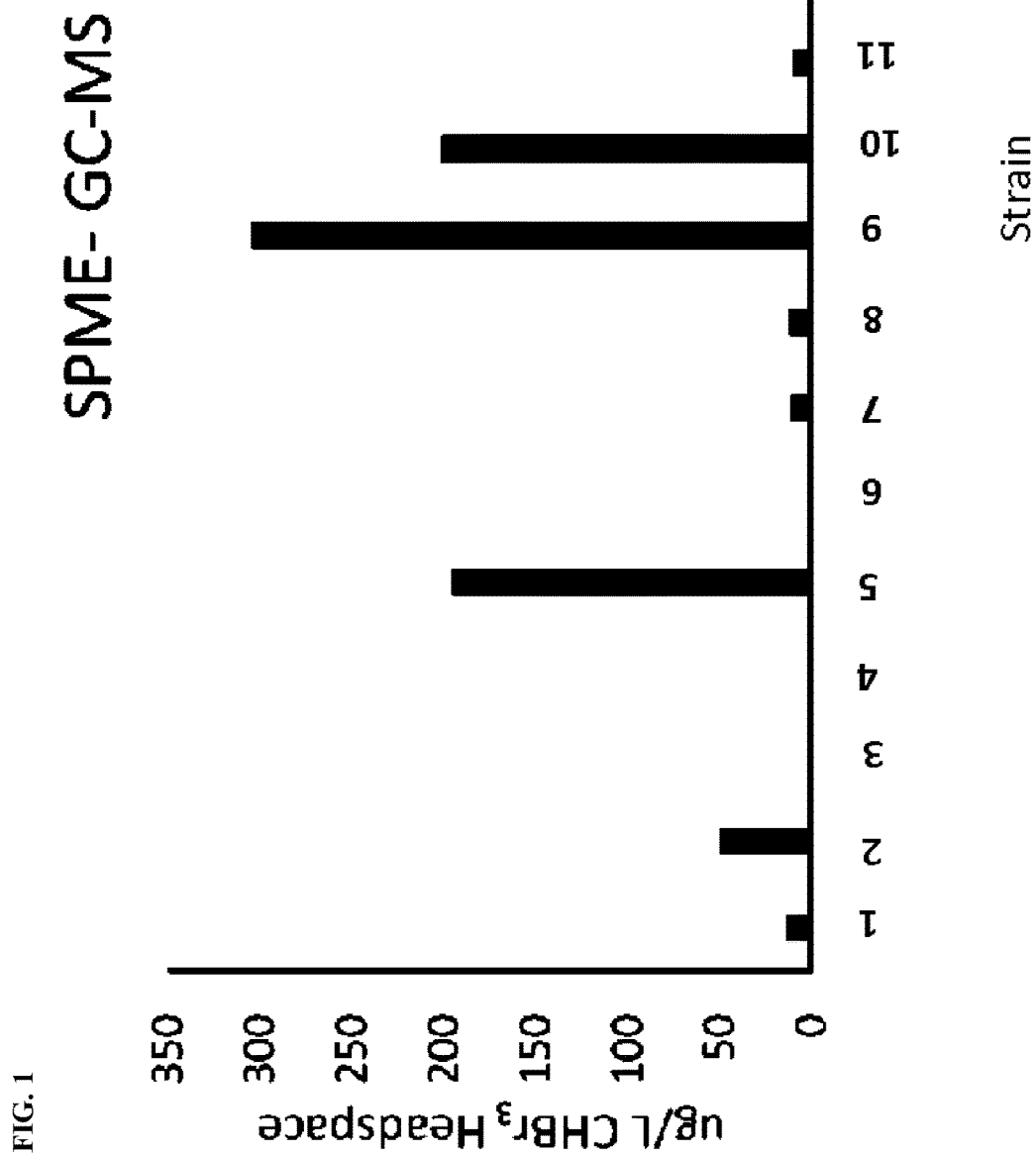
FIG. 1 depicts bromoform production assayed in 18 fungal strains including *Curvularia* sp. strain 4388 ("4388").

55 fungal cultures isolated from soil were tested via phenol red assay (each culture tested at 3 different day points). Fungal culture media and fungal biomass were tested separately. VHPO activity was quantified by absorbance measurements at 590 nm after both 2 hours and 24 hours initiation of the VHPO reaction with $H_2O_2$. The results obtained are shown in FIG. 1 for a single incubation point.

VHPO activity was detectable in most isolates with 14 isolates showing higher activity, 11 *Curvularia* and 3 *Alternaria* species. Activity was detected in both the culture media and the fungal biomass. One particular *Curvularia* isolate (Isolate 4388 also known as *Curvularia* sp. strain 4388), which showed high VHPO activity after 24 hours reaction in both the media fraction and biomass fraction, was subjected to further analysis.

For the 14 samples with high VHPO activity, including isolate 4388, more precise VHPO activity measurements were determined (i.e., enzyme kinetic assays undertaken).

Initial data collected during the optimization of the phenol red assay suggested that there was variation in VHPO rates of activity between different cultures of the same isolate. Different cultures of 4388 were pooled and used for bromoform synthesis. VHPO activity was found to be abundant in this pooled mixture after the reaction was undertaken for one week at room temperature, suggesting additional VHPO was either synthesized by the fungi or released from the biomass during this one-week bromoform synthesis reaction time.

To increase VHPO expression, the use of alternative media for isolate 4388 was investigated. The 4388 isolate was grown in triplicate cultures with different carbon sources and the VHPO activity monitored in the media. Fatty acids, glycerol, and rich complex media (PDB) did not improve or lower VHPO activity. However, increased glucose (5 g/L vs 0.5 g/L), albeit still at relatively low levels, dramatically improved both the total activity in the culture and the activity per mg of biomass. Dry mass in the increased glucose culture increased by approximately 2-fold, while VHPO activity increased by at least 20-fold.

Culture samples from isolates with VHPO activity from experiments described above were added to sealed GC-vials with KBr (20 mM), $Na_3VO_4$ (1 mM) Tris buffer (100 mM, pH 7.6) acetone (1 mM) and $H_2O_2$ (5 mM). These samples were incubated at room temperature for 1 week before analysis by GC-MS using solid-phase microextraction to monitor the presence of bromoform in the headspace. Bromoform concentration in the headspace was estimated by comparing the signals specific to bromoform with samples containing known concentrations. These results are shown in FIG. 1. Bromoform was detected in all but one of the isolates tested.

Example 2. Increased VHPO Activity in *Curvularia* sp. Strain 4388 Whole Broth Samples Fungal strains were cultured in 5 g/KL yeast extract, 1 g/L glucose, 9 uM $K_2PO4$, 5 uM $CuSO_4$, 5.5 uM $FeSO_4$, 8 uM $MgCl_2$, 5 uM $ZnSO_4$, 50 uM $Na_3VO_4$ at 28° C. at 200 rpm for 14 days. VHPO assays were conducted in 0.225 uM phenol red, 0.1 M KBr, 0.5 mM, 50 mM MOPS—pH 7.0, and initiated by the addition of 20 mM $H_2O_2$. Conversion of phenol red to bromophenol blue (measure of VHPO activity) was evaluated at an absorbance of 590 nm (bromophenol blue $\lambda_{max}$) and 430 nm (phenol red $\Delta_{max}$).

Figure 2:
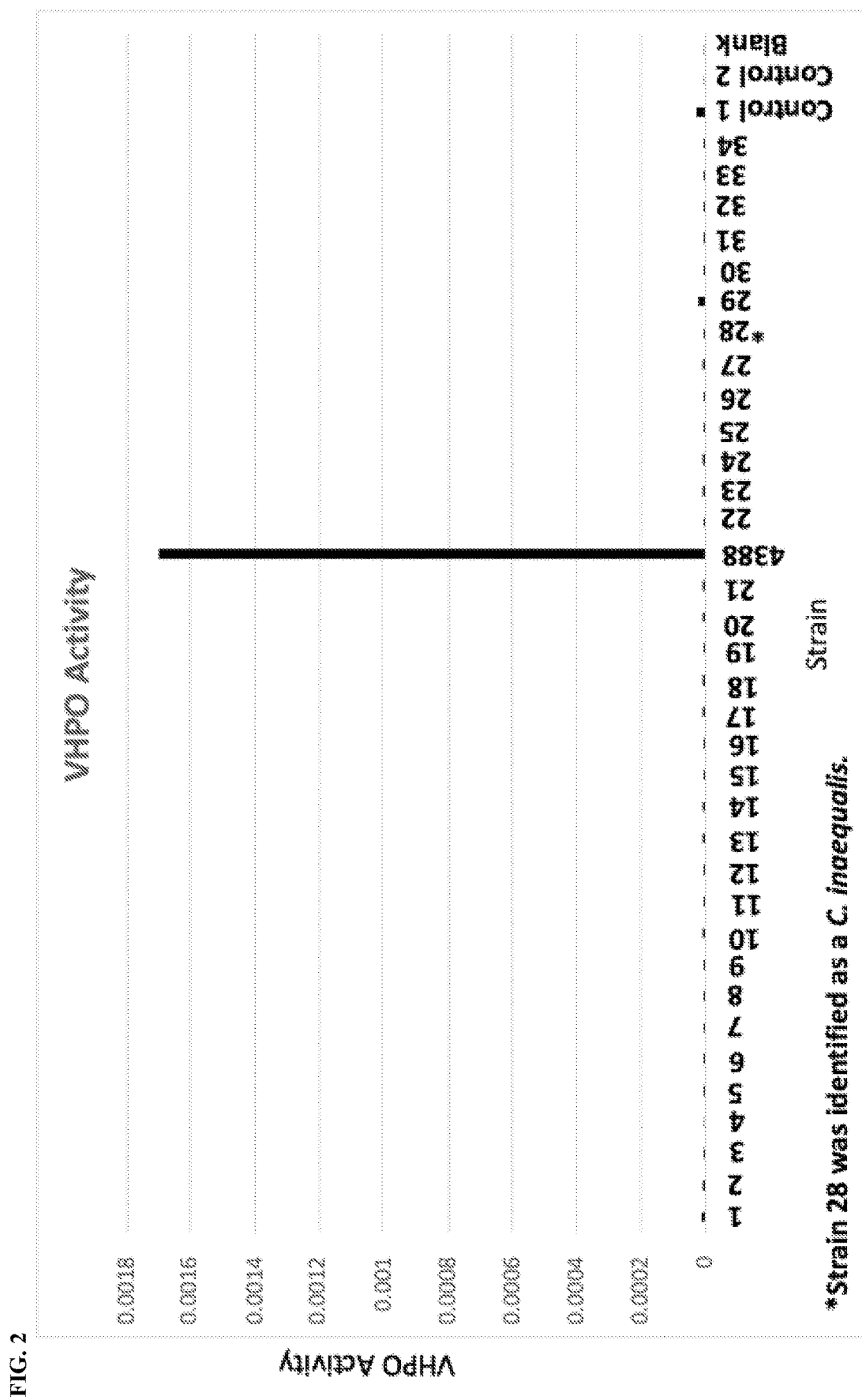
FIG. 2 depicts vanadium-dependent haloperoxidase (VHPO) activity in whole broth samples from 35 fungal strains including *Curvularia* sp. strain 4388 ("4388").

The results shown in FIG. 2 indicate that whole broth samples from *Curvularia* sp. strain 4388 had the greatest VHPO activity of any of the 35 fungal strains assayed, which included several *Curvularia* and *Alternaria* strains including *Curvularia inaequalis* strain 28.

Example 3. Increased VHPO Activity in *Curvularia* sp. Strain 4388 Biomass Samples VHPO activity from biomass samples in 55 different strains of fungi including *Curvularia* sp. strain 4388 were assayed. Most of the strains were *Curvularia* or *Alternaria*. For biomass measurements, total biomass from 15 mL cultures was rinsed with MilliQ water and freeze dried, and samples were homogenized with a steel ball bearing in a TissueLyser at 30 Hz for 2 min. The samples were then resuspended in 1 mL MilliQ water and vortexed. 100 uL of each sample was assayed for VHPO (200 uL final volume). Of particular interest was the high activity in 4388, matching well with the high activity previously observed in the media from this strain (see Table 1).

TABLE 1

VHPO activity assayed in biomass samples from 55 fungal strains including *Curvularia* sp. strain 4388.

| Strain | VHPO Activity |
| --- | --- |
| 1 | −0.000002134 |
| 2 | −0.000001816 |
| 3 | −0.000001519 |
| 4 | −0.000001437 |
| 5 | −0.000001216 |
| 6 | −0.000001027 |
| 7 | −8.64255E−07 |
| 8 | −5.62677E−07 |
| 9 | −5.49111E−07 |
| 10 | −5.28156E−07 |
| 11 | −4.54917E−07 |
| 12 | −2.48047E−07 |
| 13 | −2.40734E−07 |
| 14 | −2.31356E−07 |
| 15 | −1.79104E−07 |
| 16 | −1.61124E−07 |
| 17 | −1.60013E−07 |
| 18 | −1.18752E−07 |
| 19 | −9.3623E−08 |
| 20 | −2.359E−08 |
| 21 | −2.256E−08 |
| 22 | 3.021E−08 |
| 23 | 3.5584E−08 |
| 24 | 3.6715E−08 |
| 25 | 9.7619E−08 |
| 26 | 1.67141E−07 |
| 27 | 4.47855E−07 |
| 28 | 4.70204E−07 |
| 29 | 5.79525E−07 |
| 30 | 6.15422E−07 |
| 31 | 6.26701E−07 |
| 32 | 7.00408E−07 |
| 33 | 7.53119E−07 |
| 34 | 7.79568E−07 |
| 35 | 0.000001298 |
| 36 | 0.000001302 |
| 37 | 0.000001373 |
| 38 | 0.000001498 |
| 39 | 0.000001616 |
| 40 | 0.00000173 |
| 41 | 0.000001858 |
| 42 | 0.000001869 |
| 43 | 0.000002285 |
| 44 | 0.000002577 |
| 45 | 0.000002886 |
| 46 | 0.000002985 |
| 47 | 0.000005138 |
| 48 | 0.000010828 |
| 49 | 0.000029175 |
| 50 | 0.000029502 |
| 51 | 0.0000451 |
| 52 | 0.00005977 |
| 53 | 0.0004 |
| 54 | 0.0015 |
| 4388 | 0.0022 |

Figure 3:
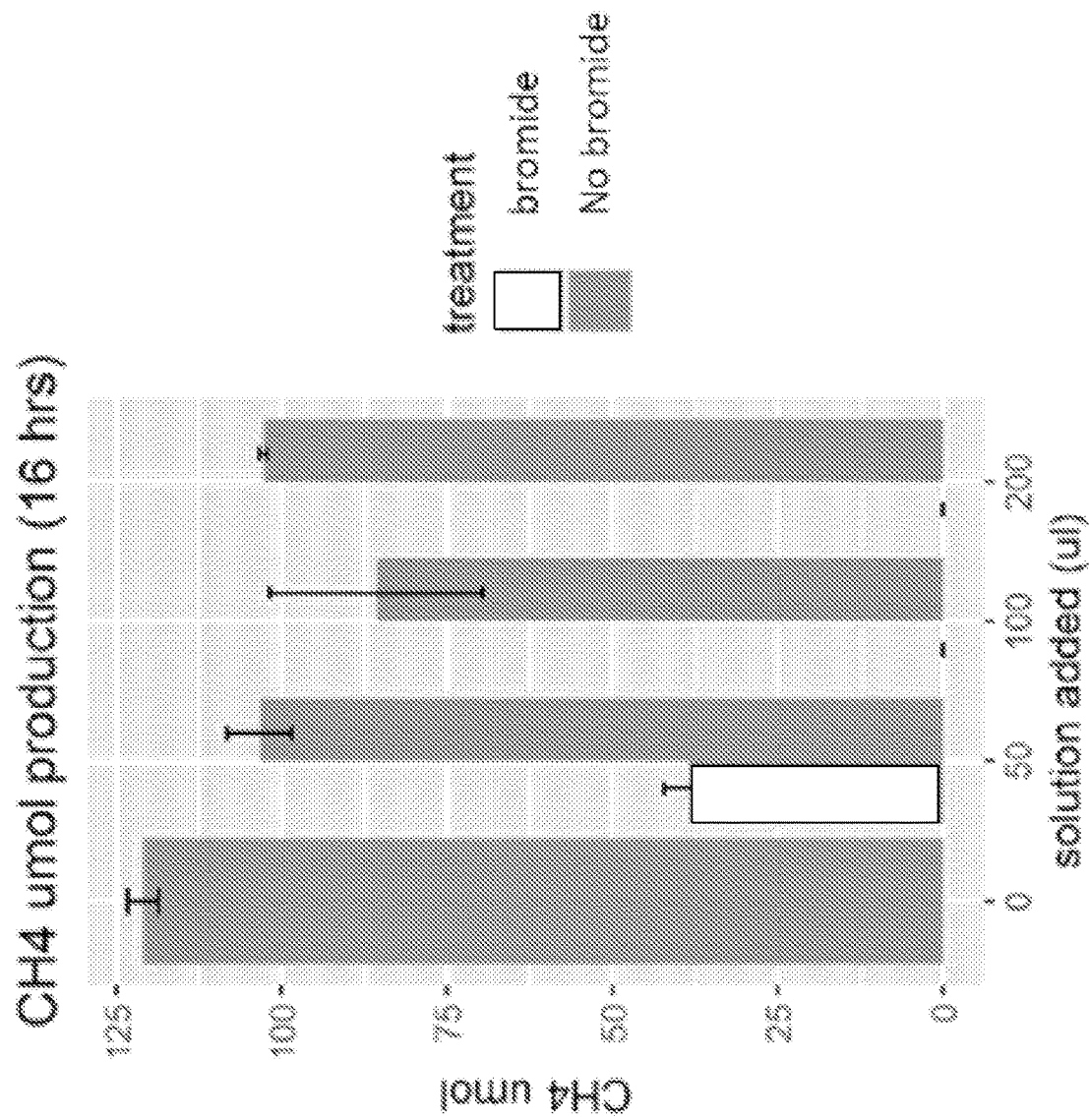
FIG. 3 depicts inhibition of methane production by Methanobrevibacter *smithii* with 0 ul, 50 ul, 100 ul, or 200 ul of *Curvularia* sp. strain 4388 culture supernatant with bromide (white bars) or without bromide (gray bars).

Example 4. *Curvularia* sp. Strain 4388 Culture Supernatant Inhibits Methanogenesis Experiments were undertaken to determine if supernatants from cultures of isolate 4388 could effectively suppress methane production by Methanobrevibacter *smithii*. Culture supernatants were taken from fungus grown in the presence of bromide (i.e., can potentially produce bromoform) and in the absence of bromide (i.e., cannot produce bromoform). In the first experiment, culture media was inoculated with *M. smithii* and culture supernatant from isolate 4388 then added. The addition of 200 ul and 100 ul of bromide culture supernatant (white bars) caused a dramatic inhibition of methane production compared with supernatants from cultures grown without bromide (gray bars) (see FIG. 3 where no significant methane production was observed with 100 ul or 200 ul of bromide culture supernatant). The lowest amount of bromide-containing culture (50 ul) also showed inhibition of methane production but less so as would be expected in a titration experiment.

Figure 4:
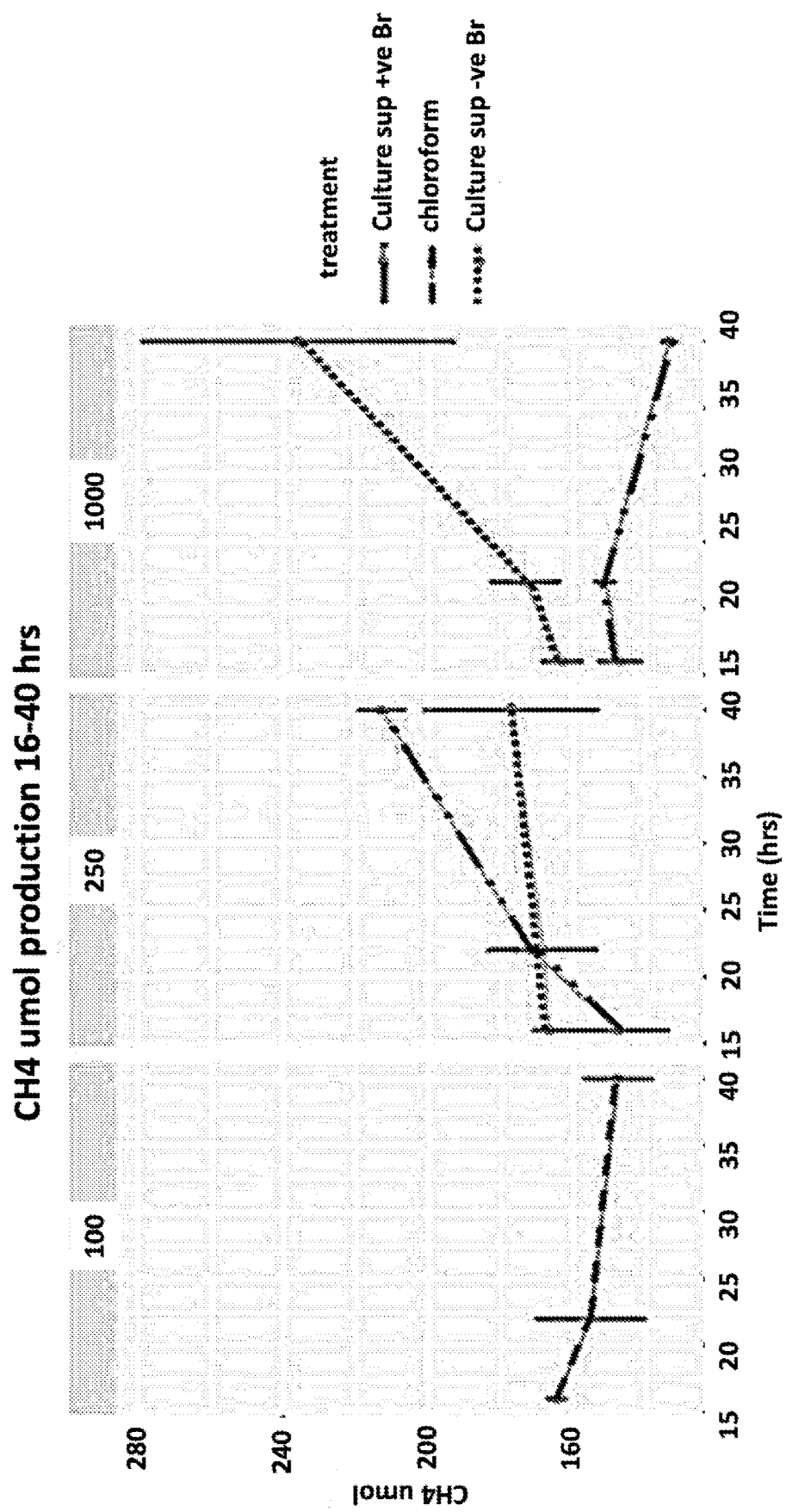
FIG. 4 depicts inhibition of methane production by Methanobrevibacter *smithii* by chloroform (positive control), *Curvularia* sp. strain 4388 culture supernatant without bromide ("Culture sup. −ve Br"; negative control), and *Curvularia* sp. strain 4388 culture supernatant with bromide ("Culture sup. +ve Br") over a 40-hour time course.

In another experiment, advanced Methanobrevibacter *smithii* cultures that had been grown for 16 hours were treated with 0, 250 ul, and 1000 ul of supernatant from bromide-containing ("+ve Br") and bromide-lacking ("−ve Br") 4388 cultures, respectively. The highest amount of bromide-containing culture (right hand graph in FIG. 4)

showed a dramatic inhibition in methane production, equivalent to the addition of 100 ul of chloroform to the culture (left hand graph in FIG. 4).

Of those tested, all but two *Curvularia* species and three *Alternaria* fungal species were shown to have VHPO enzyme activity with *Curvularia* sp. strain 4388 showing higher activity than others. Almost all cultures tested produced bromoform with differing amounts between isolates. Culture supernatants from *Curvularia* sp. strain 4388 grown in the presence of bromide were shown to significantly inhibit methane production by Methanobrevibacter *smithii* (see FIG. 4).

Example 5. Structural Characterization of VHPO from *Curvularia* sp. Strain 4388 and Methane Reduction Mechanisms The DNA and protein sequences of VHPO from *Curvularia* sp. strain 4388 were determined and are shown below. To identify the VHPO sequences the genomes were assembled using the St. Petersburg genome assembler (SPAdes). RepeatMasker was used to screen the scaffolds for interspersed repeats and low complexity DNA sequences using the DFAM database (1-8).

```
LENGTH: 1830 bp
TYPE: DNA
FEATURE: Curvularia sp. strain 4388 VHPO
                                                    SEQ ID NO: 1
ATGGGGTCCATTACACCCATCCCACTCCCTAAGATCGATGAACCCGAAGAGTATAAC

ACCAACTACATACTCTTCTGGAACCATGTCGGTTTGGAACTCAACCGCGTAACTCAC

ACTGTGGGAGGTCCCCTGACGGGACCACCTCTCTCTGCCAGGGCTCTGGGTATGCTG

CACTTGGCTATTCACGACGCATACTTTTCTATCTACCCTCCAACCGACTTCAGCACCT

TCCTCTCACCTAATGCTGAGAATGCTGCGTATCGTCTGCCCAGCCCTAATGGTGCAA

ATGATGCTCGCCAAGCAGTCGCTGGAGCTGCCCTCAAAATGCTGACTTCGCTCTACA

TGAAACCTGTAGAGACGCCTAACCCCAACCCTGGCGCTAACATCTCCGACAATGCTT

ACGCTCAGCTTGCCCTGGTTATCGACCGATCAGTTCTGAAGGCGCCCGGTGGTGTTG

ACCGAGAATCAGCCAGCTTCATGTTTGGTGAGACTGTAGCAGATGTCTTCTTTGCAC

TCCTCAACGATCCTCGAGGTGCTTCGCAGGAGGGCTACCACCCTACGCCCGGTCGCT

ATAAATTTGACGATGAACCTACCCATCCTGTCGTCCTCATTCCAGTAGACCCCAACA

ACCCCAATGGCCCCAAGAAGCCTTTCCGTCAGTACCATGCCCCATTCTACGGCAAGA

CCACGAAGCGTTTTGCCACGCAGAGCGAGCACTTCCTGGCTGACCCACCGGGTCTGC

GTTCCAATGCGGATGAGACTGCCGAGTATGATGACGCCATCCGCGTCGCTATCGCCA

TGGGCGGTGCCCAGGCCCTCAACTCCACCAAGCGTAGCCCATGGCAGACGGCACAG

GGTCTGTTCTGGGCCTATGATGGGTCAAACCTCATTGGTACACCACCTCGCTTCTAC

AACCAGATCGTACGTCGCATCGCAGTTACGTACAAGAAAGAGGAGGACCTTGCAAA

TAGCGAAGTCAACAACGCGGATTTTGCCCGCCTCTTTGCCCTCGTCGACGTTGCTTG

CACCGACGCAGGTATATTCTCCTGGAAAGAGAAGTGGGAGTATGAATTCTGGCGCC

CACTTTCCGGTGTGCGAGACGACGGACGTCCAGACCATGGAGATCCTTTCTGGCTCA

CCCTCGGTGCCCCAGCTACTAACACAAATGACATTCCATTCAAGCCTCCTTTCCCAG

CTTACCCATCTGGTCACGCGACCTTTGGCGGTGCCGTATTTCAAATGGTGCGCCGAT

ACTACAACGGCCGCGTAGGCACATGGAAGGACGACGAGCCCGACAACATCGCCATT

GACATGATGATCTCGGAGGAACTCAACGGTCTGAACCGCGACCTTCGCCAGCCCTA

CGACCCCACAGCCCCAATCGAAGACCAACCAGGTATCGTTCGTACCCGCATCGTGC

GCCACTTCGACTCTGCCTGGGAACTTATGTTCGAAAACGCCATTTCGCGTATCTTCCT

CGGCGTCCACTGGCGCTTCGATGCCGCCGCCGCACGCGACATCCTTATTCCCACTAC

GACCAAGGACGTCTACGCCGTCGACAACAACGGCGCAACTGTGTTCCAGAACGTAG

AGGATATCAGGTACACGACCAAGGGCACGCGTGAGGACCGCGAGGGTCTCTTTCCT

ATCGGCGGTGTGCCACTGGGTATCGAGATTGCGGATGAGATCTTTAACAATGGACTC

AAGCCTACACCCCCGGAGCTCCAGCCTATGCCGCAGCAGACGCCCGTGCAGAAGCC
```

```
GGTAGGTCAGCAGCCGGTTCAGGGTATGTGGGCGGAGGAGCAGGCGCCGGTGATTA

AGGAGGCGCCGTAA

LENGTH: 609 bp
TYPE: Amino Acid
FEATURE: Curvularia sp. strain 4388 VHPO
                                                  SEQ ID NO: 2
MGSITPIPLPKIDEPEEYNTNYILFWNHVGLELNRVTHTVGGPLTGPPLSARALGMLHLAI

HDAYFSIYPPTDFSTFLSPNAENAAYRLPSPNGANDARQAVAGAALKMLTSLYMKPVET

PNPNPGANISDNAYAQLALVIDRSVLKAPGGVDRESASFMFGETVADVFFALLNDPRGA

SQEGYHPTPGRYKFDDEPTHPVVLIPVDPNNPNGPKKPFRQYHAPFYGKTTKRFATQSE

HFLADPPGLRSNADETAEYDDAIRVAIAMGGAQALNSTKRSPWQTAQGLFWAYDGSNL

IGTPPRFYNQIVRRIAVTYKKEEDLANSEVNNADFARLFALVDVACTDAGIFSWKEKWE

YEFWRPLSGVRDDGRPDHGDPFWLTLGAPATNTNDIPFKPPFPAYPSGHATFGGAVFQM

VRRYYNGRVGTWKDDEPDNIAIDMMISEELNGLNRDLRQPYDPTAPIEDQPGIVRTRIV

RHFDSAWELMFENAISRIFLGVHWRFDAAAARDILIPTTTKDVYAVDNNGATVFQNVE

DIRYTTKGTREDREGLFPIGGVPLGIEIADEIFNNGLKPTPPELQPMPQQTPVQKPVGQQP

VQGMWAEEQAPVIKEAP
```

The *Curvularia inaequalis* vanadium haloperoxidase enzymatic activity and protein structure had previously been extensively studied (17-20). Vanadium haloperoxidases contain the $HVO_4^{2-}$ cofactor covalently attached to $N^2$ of His 496 while another five residues donate hydrogen bonds to the non-protein oxygens (21). The vanadium coordination site of VHPO *Curvularia inequalis* is stabilized by the amino acids: arginine 360, arginine 490, lysine 353, serine 402 and glycine 403 (21-22).

A multiple alignment of a haloperoxidase from *Curvularia inaequalis* and a VHPO from isolate 4388 was performed using Clustal omega (9). The primary amino acid sequence and the three-dimensional structural information for the haloperoxidase from *Curvularia inaequalis* was retrieved from the Protein Data Bank (PDB) (referenced herein as "*Curvularia inaequalis* PDB ID 1VNC VHPO") (10). The primary amino acid sequence of another *Curvularia inaequalis* strain (i.e., *Curvularia inaequalis* strain 28) was determined as described for isolate 4388 and is also presented below.

```
LENGTH: 609 bp
TYPE: Amino Acid
FEATURE: Curvularia inaequalis PDB ID 1VNC VHPO
                                                  SEQ ID NO: 3
MGSVTPIPLPKIDEPEEYNTNYILFWNHVGLELNRVTHTVGGPLTGPPLSARALGMLHLA

IHDAYFSICPPTDFTTFLSPDTENAAYRLPSPNGANDARQAVAGAALKMLSSLYMKPVE

QPNPNPGANISDNAYAQLGLVLDRSVLEAPGGVDRESASFMFGEDVADVFFALLNDPR

GASQEGYHPTPGRYKFDDEPTHPVVLIPVDPNNPNGPKMPFRQYHAPFYGKTTKRFATQ

SEHFLADPPGLRSNADETAEYDDAVRVAIAMGGAQALNSTKRSPWQTAQGLYWAYDG

SNLIGTPPRFYNQIVRRIAVTYKKEEDLANSEVNNADFARLFALVDVACTDAGIFSWKE

KWEFEFWRPLSGVRDDGRPDHGDPFWLTLGAPATNTNDIPFKPPFPAYPSGHATFGGAV

FQMVRRYYNGRVGTWKDDEPDNIAIDMMISEELNGVNRDLRQPYDPTAPIEDQPGIVRT
```

-continued

RIVRHFDSAWELMFENAISRIFLGVHWRFDAAAARDILIPTTTKDVYAVDNNGATVFQN

VEDIRYTTRGTREDEEGLFPIGGVPLGIEIADEIFNNGLKPTPPEIQPMPQETPVQKPVGQQ

PVKGMWEEEQAPVVKEAP

LENGTH: 604 bp
TYPE: Amino Acid
FEATURE: Curvularia inaequalis strain 28 VHPO
SEQ ID NO: 4
MGSVTPIPLPKIDEPEEYNTNYILFWNHVGLELNRVTHTVGGPLTGPPLSARALGMLHLA

IHDAYFSICPPTDFTTFLSPDAENAAYRLPSPNGANDARQAVAGAALKMLSSLYMKPIEQ

PNPNPGANISDNAYAQLGLVLDRSVLEAPGGVDRESASFMFGEAVADVFFALLNDPRG

ASQEGYHPTPGRYKFDDEPTHPVVLIPVDPNNPNGPKKPFRQYHAPFYGKTTKRFATQS

EHFLADPPGLRSNADETAEYDDAIRVAIAMGGAQALNSTKRSPWQTAQGLYWAYDGS

NLIGTPPRFYNQIVRRIAVTYKKEEDLANSEVNNADFARLFALVDVACTDAGIFSWKEK

WEFEFWRPLSGVRDDGRPDHGDPFWLTLGAPATNTNDIPFKPPFPAYPSGHATFGGAVF

QMVRRYYNGRVGTWKDDEPDNIAIDMMISEELNGLNRDLRQPYDPTAPIEDQPGIVRTR

IVRHFDSAWELMFENAISRIFLGVHWRFDAAAARDILIPTTTKDVYAVDNNGATVFQNV

EDIRYTTKGTREDREGLFPIGGVPLGIEIANEIFNNGLKPTPPEIQPMPQETPVQEPVKGM

WEEEQAPIIKEAP

A Clustal Omega Alignment of *Curvularia* sp. strain 4388 VHPO and the *Curvularia inaequalis* PDB ID 1VNC VHPO is presented in FIG. 5. To further evaluate amino acid substitutions responsible for the increased VHPO activity in *Curvularia* sp. strain 4388 VHPO, a Clustal Omega Alignment of *Curvularia* sp. strain 4388 VHPO, *Curvularia inaequalis* PDB ID 1VNC VHPO, and *Curvularia inaequalis* strain 28 VHPO was performed (see FIG. 6).

TABLE 2

Amino acid variations between *Curvularia* sp. strain 4388 VHPO and *Curvularia inaequalis* PDB ID 1VNC VHPO. The following substitutions were found when comparing the two sequences. Amino acid substitutions shown in bold font were present in *Curvularia* sp. strain 4388 VHPO while the corresponding amino acid residues were conserved in both *Curvularia inaequalis* PDB ID 1VNC VHPO and *Curvularia inaequalis* strain 28 VHPO (see FIG. 6).

| Position | *Curvularia inaequalis* PDB ID 1VNC | *Curvularia* sp. strain 4388 |
|---|---|---|
| 3 | Val | Ile |
| 69 | Cys | Tyr |
| 75 | Thr | Ser |
| 81 | Asp | Asn |
| 82 | Thr | Ala |
| 111 | Ser | Thr |
| 120 | Gln | Thr |
| 138 | Gly | Ala |
| 141 | Leu | Ile |
| 147 | Glu | Lys |
| 163 | Asp | Thr |
| 215 | Met | Lys |
| 261 | Val | Ile |
| 288 | Tyr | Phe |
| 356 | Phe | Tyr |
| 447 | Val | Leu |
| 538 | Arg | Lys |
| 544 | Glu | Arg |
| 575 | Ile | Leu |
| 581 | Glu | Gln |

TABLE 2-continued

Amino acid variations between *Curvularia* sp. strain 4388 VHPO and *Curvularia inaequalis* PDB ID 1VNC VHPO. The following substitutions were found when comparing the two sequences. Amino acid substitutions shown in bold font were present in *Curvularia* sp. strain 4388 VHPO while the corresponding amino acid residues were conserved in both *Curvularia inaequalis* PDB ID 1VNC VHPO and *Curvularia inaequalis* strain 28 VHPO (see FIG. 6).

| Position | *Curvularia inaequalis* PDB ID 1VNC | *Curvularia* sp. strain 4388 |
|---|---|---|
| 594 | Lys | Gln |
| 598 | Glu | Ala |
| 605 | Val | Ile |

A Clustal Omega Alignment of the amino acid sequence of *Curvularia* sp. strain 4388 VHPO with the amino acid sequences of VHPO from twelve representative strains selected from those evaluated in FIG. 2 including *Curvularia inaequalis* strain 28 was performed (data not shown). This analysis further confirmed amino acid differences responsible for the enhanced VHPO activity observed in *Curvularia* sp. strain 4388. The following unique amino acid variations were only present in *Curvularia* sp. strain 4388 VHPO and not in the VHPO from any of the twelve representative fungal strains: tyrosine at position 69, threonine at position 120, threonine at position 163, and glutamine at position 581.

The three-dimensional structural data of *Curvularia* sp. strain 4388 VHPO was determined by Alphafold (11). The structure is mainly helical, a small part of β-structures, and the rest are loops. We determined disordered loops in region 120-129, 180-195, 201-222, 450-463 and 567-609 by using IUPRED (12) (see FIGS. 7 and 8A-8C).

A molecular weight of 67.56 kDa and an isoelectric point of 5.11 for the *Curvularia* sp. strain 4388 VHPO were determined by Expasy (13).

The structural similarity of *Curvularia* sp. strain 4388 VHPO with *Curvularia inaequalis* PDB ID 1VNC VHPO was determined using an alignment in pymol (14) (see FIG. 9). The root mean deviation square between the two proteins is 0.308.

The structural conservation of the vanadate binding site in *Curvularia* sp. strain 4388 VHPO was determined and compared with the structure of *Curvularia inaequalis* PDB ID 1VNC VHPO. Histidine 496, arginine 360, arginine 490, serine 402, and histidine 404 are conserved and are amino acids that are involved in the covalent binding of vanadate with VHPO (see FIG. 10).

*Curvularia* sp. strain 4388 VHPO contains 23 amino acid variations when compared to *Curvularia inaequalis* PDB ID 1VNC VHPO. The location of these variations was determined in the three-dimensional structure, and it was found that the vanadate binding site is conserved. Three amino acid variations are located on the surface of the protein (i.e., tyrosine 69, phenylalanine 288, and tyrosine 356) and are aromatic residues that have been previously showed to be bound to bromide (see FIG. 11). Bromination of surface exposed aromatic residues is one of the mechanisms that promote haloperoxidase activity.

Another mechanism implicated in haloperoxidase activity is related to dimerization of monomeric VHPO subunits. The dimeric conformation of *Curvularia* sp. strain 4388 VHPO was determined by using Alphafold multimer (15). The three-dimensional structure of the dimeric conformation shows asymmetric binding mediated by short loop regions and short beta pleated conformations (see FIG. 12). Dimerization of *Curvularia* sp. strain 4388 VHPO increases stability and VHPO activity by adding two vanadate active sites in one dimeric complex.

The solvent accessible surface area (SASA) for *Curvularia* sp. strain 4388 VHPO was predicted and compared to *Curvularia inaequalis* PDB ID 1VNC VHPO.

$$\textit{Curvularia} \text{ sp. strain 4388 } \textit{VHPO SASA } (nm^2) = 326.21$$

$$\textit{Curvularia inaequalis} \text{ PDB ID 1VNC VHPO SASA } (nm^2) = 245.674$$

The three-dimensional structure of *Curvularia* sp. strain 4388 VHPO was energy minimized (steepest descent method) and solvated with water molecules and neutralized with $Na^+$ and $Br^-$ in an orthorhombic cell (16). The presence of a flexible loop at the carboxy terminal region modulates haloperoxidase activity by modifying solvation rate and interacting with bromide ($Br^-$) species (see FIG. 13).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES

1. Hubley R, Finn R D, Clements J, Eddy S R, Jones T A, Bao W, et al. The Dfam database of repetitive DNA families. Nucleic Acids Res. 2016 Jan. 4; 44 (D1):D81-9.
2. Flynn J M, Hubley R, Goubert C, Rosen J, Clark A G, Feschotte C, et al. RepeatModeler2: automated genomic discovery of transposable element families [Internet]. Genomics; 2019 November [cited 2022 Apr. 22]. Available from: http://biorxiv.org/lookup/doi/10.1101/856591). After softmasking the repeats, the Funannotate pipeline was used to predicted protein coding genes (https://funannotate.readthedocs.io/en/latest/). A number of ab initio gene predictors, including: Augustus, snap, glimmerHMM, CodingQuarry and GeneMark-ES/ET are run (Korf I. Gene finding in novel genomes. BMC Bioinformatics. 2004 May 14; 5(1):59. TigrScan and GlimmerHMM: two open source ab initio eukaryotic gene-finders| Bioinformatics| Oxford Academic [Internet]. [cited 2022 Apr. 22]. Available from: https://academic.oup.com/bioinformatics/article/20/16/2878/236797
3. Testa A C, Hane J K, Ellwood S R, Oliver R P. CodingQuarry: highly accurate hidden Markov model gene prediction in fungal genomes using RNA-seq transcripts. BMC Genomics. 2015 Mar. 11; 16(1):170.
4. Borodovsky M, Lomsadze A. Eukaryotic Gene Prediction Using GeneMark.hmm-E and GeneMark-ES. Curr Protoc Bioinforma Ed Board Andreas Baxevanis Al. 2011 September; CHAPTER:Unit.
5. Hoff K J, Stanke M. Predicting Genes in Single Genomes with AUGUSTUS. Curr Protoc Bioinforma. 2019; 65 (1):e57.
6. Brůna T, Hoff K J, Lomsadze A, Stanke M, Borodovsky M. BRAKER2: automatic eukaryotic genome annotation with GeneMark-EP+ and AUGUSTUS supported by a protein database. NAR Genomics Bioinforma [Internet]. 2021 Mar. 1 [cited 2021 Aug. 24]; 3 (1). Available from: https://doi.org/10.1093/nargab/lqaa108
7. Buchfink B, Xie C, Huson D H. Fast and sensitive protein alignment using DIAMOND. Nat Methods. 2015 January; 12(1):59-60.
8. Gotoh O. Direct mapping and alignment of protein sequences onto genomic sequence. Bioinformatics. 2008 Nov. 1; 24(21):2438-44). Finally, Evidence Modeler will take in all models to create a weighted consensus gene mode Automated eukaryotic gene structure annotation using EVidenceModeler and the Program to Assemble Spliced Alignments Genome Biology| Full Text [Internet]. [cited 2022 Apr. 22]. Available from: https://genomebiology.biomedcentral.com/articles/10.1186/gb-2008-9-1-r7).
9. Sievers et al., "Fast, Scalable Generation of High-quality Protein Multiple Sequence Alignments Using Clustal Omega.".
10. PDB-101: Educational resources supporting molecular explorations through biology and medicine. Christine Zardecki, Shuchismita Dutta, David S. Goodsell, Robert Lowe, Maria Voigt, Stephen K. Burley. (2022) Protein Science 31: 129-140 doi:10.1002/pro.4200
11. Jumper, J et al. Highly accurate protein structure prediction with AlphaFold. Nature (2021)
12. Bálint Mészáros, Gábor Erdős, Zsuzsanna Dosztányi, IUPred2A: context-dependent prediction of protein disorder as a function of redox state and protein binding, Nucleic Acids Research, 2018; 46 (W1):W329-W337
13. (Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005))
14. The PyMOL Molecular Graphics System, Version 2.0 Schrödinger, LLC
15. Evans et al., "Protein Complex Prediction with AlphaFold-Multimer."

16. Paul Bauer, Berk Hess, & Erik Lindahl. (2022). GROMACS 2022.2 Manual (2022.2). Zenodo. https://doi.org/10.5281/zenodo.6637572
17. Van Schijndel, J. W. P. M., Barnett, P., Roelse, J., Vollenbroek, E. G. M. and Wever, R. (1994), The Stability and Steady-State Kinetics of Vanadium Chloroperoxidase from the Fungus *Curvularia Inaequalis*. European Journal of Biochemistry, 225: 151-157. https://doi.org/10.1111/j.1432-1033.1994.00151.x
18. Dong, J. J., et al., Halofunctionalization of alkenes by vanadium chloroperoxidase from *Curvularia inaequalis*, Chem. Commun., 2017, 53, 6207
19. Hilda B ten Brink, Henk L Dekker, Hans E Schoemaker, Ron Wever, Oxidation reactions catalyzed by vanadium chloroperoxidase from *Curvularia inaequalis*, Journal of Inorganic Biochemistry, Volume 80, Issues 1-2, 2000, Pages 91-98, ISSN 0162-0134, https://doi.org/1001016/S0162-0134(00)00044-1
20. Messerschmidt, A. et al., X-ray structure of a vanadium containing enzyme: Chloroperoxidase from the fungus *Curvularia inaequalis*, Proc. Natl. Acad. Sci. USA, Vol. 93, pp. 392-396, January 1996 Biochemistry
21. Renirie, R., Hemrika, W., Piersma, S. R., & Wever, R. (2000). Cofactor and Substrate Binding to Vanadium Chloroperoxidase Determined by UV-VIS Spectroscopy and Evidence for High Affinity for Pervanadate †. Biochemistry, 39(5), 1133-1141. https://doi.org/10.1021/bi9221790
22. Hemrika, W., Renirie, R., Macedo-Ribeiro, S., Messerschmidt, A., & Wever, R. (1999). Heterologous Expression of the Vanadium-containing Chloroperoxidase from *Curvularia inaequalis* in *Saccharomyces cerevisiae* and Site-directed Mutagenesis of the Active Site Residues His496, Lys353, Arg360, and Arg490. Journal of Biological Chemistry, 274(34), 23820-23827. https://dio.org/10.1074/jbc.274.34.23820
23. Thapa, H. R., Lin, Z., Yi, D., Smith, J. E., Schmidt, E. W., & Agarwal, V. (2020). Genetic and Biochemical Reconstitution of Bromoform Biosynthesis in *Asparagopsis* Lends Insights into Seaweed Reactive Oxygen Species Enzymology. ACS Chemical Biology, 15(6), 1662-1670. https://dio.org/10.1021/schembio.0e00299
24. Machado, L., Magnusson, M., Paul, N. A., de Nys, R., & Tomkins, N. (2014). Effects of Marine and Freshwater Macroalgae on In Vitro Total Gas and Methane Production. PLOS ONE, 9(1), e85289. https://dio.org/10.1371/journal.pone.0085289
25. Roque, B. M., Brooke, C. G., Ladau, J., Polley, T., Marsh, L. J., Najafi, N., Pandey, P., Singh, L., Kinley, R., Salwen, J. K., Eloe-Fadrosh, E., Kebreab, E., & Hess, M. (2019). Effect of the macroalgae *Asparagopsis taxiformis* on methane production and rumen microbiome assemblage. Animal Microbiome, 1(1), 3. https://doi.org/10.1186/s42523-019-0004-4
26. Machado, L., Magnusson, M., Paul, N. A., Kinley, R., de Nys, R., & Tomkins, N. (2016). Identification of bioactives from the red seaweed *Asparagopsis taxiformis* that promote antimethanogenic activity in vitro. Journal of Applied Phycology, 28(5), 3117-3126. https://doi.org/10.1007/s10811-016-0830-7
27. Goel, G., Makkar, H. P. S., & Becker, K. (2009). Inhibition of methanogens by bromochloromethane: Effects on microbial communities and rumen fermentation using batch and continuous fermentations. British Journal of Nutrition, 101(10), 1484. https://dio.org/10.1017/S0007114508076198
28. Honan, M., Feng, X., Tricarico, J. M., & Kebreab, E. (2021). Feed additives as a strategic approach to reduce enteric methane production in cattle: Modes of action, effectiveness and safety. Animal Production Science. https://doi.org/10.1071/AN20295

SEQUENCE LISTING

```
Sequence total quantity: 4
SEQ ID NO: 1            moltype = DNA  length = 1830
FEATURE                 Location/Qualifiers
source                  1..1830
                        mol_type = other DNA
                        organism = synthetic construct
SEQUENCE: 1
atggggtcca ttacacccat cccactccct aagatcgatg aacccgaaga gtataacacc   60
aactacatac tcttctggaa ccatgtcggt ttggaactca accgcgtaac tcacactgtg  120
ggaggtcccc tgacgggacc acctctctct gccagggctc tgggtatgct gcacttggct  180
attcacgacg catacttttc tatctaccct ccaaccgact tcagcacctt cctctcacct  240
aatgctgaga atgctgcgta tcgtctgccc agccctaatg gtgcaaatga tgctcgccaa  300
gcagtcgctg gagctgccct caaaatgctg acttcgctct acatgaaacc tgtagagacg  360
cctaacccca accctggcgc taacatctcc gacaatgctt acgctcagct tgccctggtt  420
atcgaccgat cagttctgaa ggcgcccggt ggtgttgacc gagaatcagc cagcttcatg  480
tttggtgaga ctgtagcaga tgtcttcttt gcactcctca acgatcctcg aggtgcttcg  540
caggagggct accaccctac gcccggtcgc tataaatttg acgatgaacc tacccatcct  600
gtcgtcctca ttccagtaga ccccaacaac cccaatggcc caagaagcc tttccgtcag  660
taccatgccc cattctacgg caagaccacg aagcgttttg ccacgcagag cgagcacttc  720
ctggctgacc caccgggtct gcgttccaat gcggatgaga ctgccgagta tgatgacgcc  780
atccgcgtcg ctatcgccat gggcggtgcc caggccctca actccaccaa gcgtagccca  840
tggcagacgg cacagggtct gttctggccc tatgatgggt caaacctcat tggtacacca  900
cctcgcttct acaaccagat cgtacgtcgc atcgcagtta cgtacaagaa agaggaggac  960
cttgcaaata gcgaagtcaa caacgcggat tttgcccgcc tcttttgccct cgtcgacgtt 1020
gcttgcaccg acgcaggtat attctcctgg aaagagaagt gggagtatga attctggcgc 1080
ccactttccg gtgtgcgaga cgacggacgt ccagaccatg gagatccttt ctggctcacc 1140
ctcggtgccc cagctactaa cacaaatgac attccattca agcctccttt cccagcttac 1200
ccatctggtc acgcgaccct tggcggtgcc gtatttcaaa tggtgcgccg atactacaac 1260
ggccgcgtag gcacatggaa ggacgacgag cccgacaaca tcgccattga catgatgatc 1320
tcggaggaac tcaacggtct gaaccgcgac cttcgccagc cctacgaccc cacagcccca 1380
atcgaagacc aaccaggtat cgttcgtacc cgcatcgtgc gccacttcga ctctgcctgg 1440
gaacttatgt tcgaaacgc catttcgcgt atcttcctcg gcgtccactg gcgcttcgat 1500
gccgccgccg cacgcgacat ccttattccc actacgacca aggacgtcta cgccgtcgac 1560
```

```
aacaacggcg caactgtgtt ccagaacgta gaggatatca ggtacacgac caagggcacg   1620
cgtgaggacc gcgagggtct ctttcctatc ggcggtgtgc cactgggtat cgagattgcg   1680
gatgagatct ttaacaatgg actcaagcct acaccccggg agctccagcc tatgccgcag   1740
cagacgcccg tgcagaagcc ggtaggtcag cagccggttc agggtatgtg ggcggaggag   1800
caggcgccgg tgattaagga ggcgccgtaa                                    1830

SEQ ID NO: 2            moltype = AA  length = 609
FEATURE                 Location/Qualifiers
source                  1..609
                        mol_type = protein
                        organism = synthetic construct
SEQUENCE: 2
MGSITPIPLP KIDEPEEYNT NYILFWNHVG LELNRVTHTV GGPLTGPPLS ARALGMLHLA    60
IHDAYFSIYP PTDFSTFLSP NAENAAYRLP SPNGANDARQ AVAGAALKML TSLYMKPVET   120
PNPNPGANIS DNAYAQLALV IDRSVLKAPG GVDRESASFM FGETVADVFF ALLNDPRGAS   180
QEGYHPTPGR YKFDDEPTHP VVLIPVDPNN PNGPKKPFRQ YHAPFYGKTT KRFATQSEHF   240
LADPPGLRSN ADETAEYDDA IRVAIAMGGA QALNSTKRSP WQTAQGLFWA YDGSNLIGTP   300
PRFYNQIVRR IAVTYKKEED LANSEVNNAD FARLFALVDV ACTDAGIFSW KEKWEYEFWR   360
PLSGVRDDGR PDHGDPFWLT LGAPATNTND IPFKPPFPAY PSGHATFGGA VFQMVRRYYN   420
GRVGTWKDDE PDNIAIDMMI SEELNGLNRD LRQPYDPTAP IEDQPGIVRT RIVRHFDSAW   480
ELMFENAISR IFLGVHWRFD AAAARDILIP TTTKDVYAVD NNGATVFQNV EDIRYTTKGT   540
REDREGLFPI GGVPLGIEIA DEIFNNGLKP TPPELQPMPQ QTPVQKPVGQ QPVQGMWAEE   600
QAPVIKEAP                                                           609

SEQ ID NO: 3            moltype = AA  length = 609
FEATURE                 Location/Qualifiers
source                  1..609
                        mol_type = protein
                        organism = synthetic construct
SEQUENCE: 3
MGSVTPIPLP KIDEPEEYNT NYILFWNHVG LELNRVTHTV GGPLTGPPLS ARALGMLHLA    60
IHDAYFSICP PTDFTTFLSP DTENAAYRLP SPNGANDARQ AVAGAALKML SSLYMKPVEQ   120
PNPNPGANIS DNAYAQLGLV LDRSVLEAPG GVDRESASFM FGEDVADVFF ALLNDPRGAS   180
QEGYHPTPGR YKFDDEPTHP VVLIPVDPNN PNGPKMPFRQ YHAPFYGKTT KRFATQSEHF   240
LADPPGLRSN ADETAEYDDA VRVAIAMGGA QALNSTKRSP WQTAQGLYWA YDGSNLIGTP   300
PRFYNQIVRR IAVTYKKEED LANSEVNNAD FARLFALVDV ACTDAGIFSW KEKWEFEFWR   360
PLSGVRDDGR PDHGDPFWLT LGAPATNTND IPFKPPFPAY PSGHATFGGA VFQMVRRYYN   420
GRVGTWKDDE PDNIAIDMMI SEELNGVNRD LRQPYDPTAP IEDQPGIVRT RIVRHFDSAW   480
ELMFENAISR IFLGVHWRFD AAAARDILIP TTTKDVYAVD NNGATVFQNV EDIRYTTRGT   540
REDEEGLFPI GGVPLGIEIA DEIFNNGLKP TPPEIQPMPQ ETPVQKPVGQ QPVKGMWEEE   600
QAPVVKEAP                                                           609

SEQ ID NO: 4            moltype = AA  length = 604
FEATURE                 Location/Qualifiers
source                  1..604
                        mol_type = protein
                        organism = synthetic construct
SEQUENCE: 4
MGSVTPIPLP KIDEPEEYNT NYILFWNHVG LELNRVTHTV GGPLTGPPLS ARALGMLHLA    60
IHDAYFSICP PTDFTTFLSP DAENAAYRLP SPNGANDARQ AVAGAALKML SSLYMKPIEQ   120
PNPNPGANIS DNAYAQLGLV LDRSVLEAPG GVDRESASFM FGEAVADVFF ALLNDPRGAS   180
QEGYHPTPGR YKFDDEPTHP VVLIPVDPNN PNGPKKPFRQ YHAPFYGKTT KRFATQSEHF   240
LADPPGLRSN ADETAEYDDA IRVAIAMGGA QALNSTKRSP WQTAQGLYWA YDGSNLIGTP   300
PRFYNQIVRR IAVTYKKEED LANSEVNNAD FARLFALVDV ACTDAGIFSW KEKWEFEFWR   360
PLSGVRDDGR PDHGDPFWLT LGAPATNTND IPFKPPFPAY PSGHATFGGA VFQMVRRYYN   420
GRVGTWKDDE PDNIAIDMMI SEELNGLNRD LRQPYDPTAP IEDQPGIVRT RIVRHFDSAW   480
ELMFENAISR IFLGVHWRFD AAAARDILIP TTTKDVYAVD NNGATVFQNV EDIRYTTKGT   540
REDREGLFPI GGVPLGIEIA NEIFNNGLKP TPPEIQPMPQ ETPVQEPVKG MWEEEQAPII   600
KEAP                                                                604
```

What is claimed is:

1. A method for reducing methane emissions from a ruminant, the method comprising administering to the ruminant bromoform produced by a composition comprising: bromide, and a vanadium-dependent haloperoxidase (VHPO) comprising SEQ ID NO: 2; thereby reducing methane emissions in the ruminant relative to a ruminant not administered bromoform produced by the composition.

2. The method of claim 1, wherein the VHPO is expressed by a fungal strain belonging to the genus *Curvularia*.

3. The method of claim 1, wherein the ruminant is a member of the family Bovidae.

4. The method of claim 3, wherein the ruminant is *Bos taurus*.

5. The method of claim 2, wherein the fungal strain is *Curvularia* sp. strain 4388 (NMI Accession No. V22/011149).

* * * * *